(12) United States Patent
Null et al.

(10) Patent No.: US 10,314,621 B2
(45) Date of Patent: Jun. 11, 2019

(54) LAMINOPLASTY DEVICES AND METHODS

(71) Applicant: WARSAW ORTHOPEDIC, INC., Warsaw, IN (US)

(72) Inventors: William B. Null, Olive Branch, MS (US); Robert W. Weakley, Collierville, TN (US); Gregory C. Marik, Germantown, TN (US); John G. Heller, Atlanta, GA (US); Jeffrey C. Wang, Sherman Oaks, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 324 days.

(21) Appl. No.: 14/162,872

(22) Filed: Jan. 24, 2014

(65) Prior Publication Data

US 2014/0135845 A1 May 15, 2014

Related U.S. Application Data

(60) Continuation of application No. 12/386,892, filed on Apr. 24, 2009, now abandoned, which is a division of application No. 10/447,126, filed on May 28, 2003, now Pat. No. 8,105,366.

(60) Provisional application No. 60/384,573, filed on May 30, 2002.

(51) Int. Cl.
*A61B 17/80* (2006.01)
*A61B 17/70* (2006.01)

(52) U.S. Cl.
CPC ...... *A61B 17/7059* (2013.01); *A61B 17/7071* (2013.01)

(58) Field of Classification Search
CPC .......................... A61B 17/7071; A61B 17/58; A61B 17/7044; A61B 17/7059; A61B 17/80; A61B 17/7056; A61B 17/7047; A61B 17/7062; A61B 90/10; A61B 17/64; A61B 17/809; A61B 17/8042; A61B 17/8047; A61B 17/8033; A61F 2/4611; A61F 2002/30841; F16B 37/14
USPC ....................................................... 606/130
See application file for complete search history.

(56) References Cited

U.S. PATENT DOCUMENTS

| 2,599,551 A | 6/1952 | Hagen |
| 3,716,050 A | 2/1973 | Johnston |
| 4,013,078 A | 3/1977 | Feild |
| 4,454,876 A | 6/1984 | Mears |

(Continued)

FOREIGN PATENT DOCUMENTS

| CA | 2351231 A1 | 12/2001 |
| EP | 1 103 236 A2 | 5/2001 |

(Continued)

OTHER PUBLICATIONS

Abstract of FR 2783411.*

(Continued)

*Primary Examiner* — Brian E Pellegrino

(57) ABSTRACT

Laminoplasty plates are engageable to at least one portion of a divided lamina to maintain a desired spacing relative to the spinal canal. The laminoplasty plates include a spacer portion having a first end and a second end that spans a gap formed by at least one of a divided lamina portion. The laminoplasty plates can include a lamina engagement portion at one end for engagement with the divided lamina portion.

6 Claims, 23 Drawing Sheets

(56) References Cited

U.S. PATENT DOCUMENTS

| | | | |
|---|---|---|---|
| 4,479,491 A | 10/1984 | Martin | |
| 4,611,582 A | 9/1986 | Duff | |
| 4,800,874 A | 1/1989 | David et al. | |
| 4,838,252 A | 6/1989 | Klaue | |
| 4,867,144 A | 9/1989 | Karas et al. | |
| 5,002,544 A | 3/1991 | Klaue et al. | |
| 5,057,111 A | 10/1991 | Park | |
| 5,133,718 A | 7/1992 | Mao | |
| 5,190,544 A | 3/1993 | Chapman et al. | |
| 5,304,178 A | 4/1994 | Stahurski | |
| 5,304,180 A | 4/1994 | Slocum | |
| 5,318,567 A | 6/1994 | Vichard | |
| 5,372,598 A | 12/1994 | Luhr et al. | |
| 5,437,672 A | 8/1995 | Alleyne | |
| 5,487,741 A | 1/1996 | Maruyama et al. | |
| 5,496,318 A | 3/1996 | Howland et al. | |
| 5,527,312 A | 6/1996 | Ray | |
| 5,618,288 A * | 4/1997 | Calvo | A61B 90/14 606/130 |
| 5,645,599 A | 7/1997 | Samani | |
| 5,662,655 A | 9/1997 | Laboureau et al. | |
| 5,676,667 A | 10/1997 | Hausman | |
| 5,681,311 A | 10/1997 | Foley et al. | |
| 5,709,682 A | 1/1998 | Medoff | |
| 5,709,686 A | 1/1998 | Talos et al. | |
| 5,785,712 A | 7/1998 | Runciman et al. | |
| 5,941,878 A | 8/1999 | Medoff | |
| 5,951,557 A | 9/1999 | Luter | |
| 5,980,572 A | 11/1999 | Kim et al. | |
| 6,001,130 A | 12/1999 | Bryan et al. | |
| 6,045,552 A | 4/2000 | Zucherman et al. | |
| 6,080,157 A | 6/2000 | Cathro et al. | |
| 6,156,037 A | 12/2000 | LeHuec et al. | |
| 6,174,311 B1 * | 1/2001 | Branch | A61F 2/4611 606/86 A |
| 6,358,254 B1 | 3/2002 | Anderson | |
| 6,419,703 B1 | 7/2002 | Fallin et al. | |
| 6,520,990 B1 | 2/2003 | Ray | |
| 6,572,617 B1 | 6/2003 | Senegas | |
| 6,626,944 B1 | 9/2003 | Taylor | |
| 6,635,087 B2 | 10/2003 | Angelucci et al. | |
| 6,660,007 B2 | 12/2003 | Khanna | |
| 6,712,852 B1 | 3/2004 | Chung et al. | |
| 6,746,450 B1 * | 6/2004 | Wall | A61B 17/7059 606/280 |
| 6,776,800 B2 | 8/2004 | Boyer, II et al. | |
| 6,997,953 B2 | 2/2006 | Chung et al. | |
| 2002/0029039 A1 * | 3/2002 | Zucherman | A61B 17/7068 606/249 |
| 2002/0120335 A1 | 8/2002 | Angelucci et al. | |
| 2002/0128654 A1 | 9/2002 | Steger et al. | |
| 2003/0045935 A1 | 3/2003 | Angelucci et al. | |
| 2003/0045936 A1 | 3/2003 | Angelucci et al. | |
| 2003/0050700 A1 | 3/2003 | Kihara | |
| 2003/0125738 A1 | 7/2003 | Khanna | |
| 2003/0199875 A1 | 10/2003 | Mingozzi et al. | |
| 2004/0030388 A1 | 2/2004 | Null et al. | |
| 2004/0153155 A1 | 8/2004 | Chung et al. | |
| 2004/0210222 A1 | 10/2004 | Angelucci et al. | |
| 2005/0107877 A1 | 5/2005 | Blain | |
| 2005/0131412 A1 | 6/2005 | Olevsky et al. | |
| 2005/0197700 A1 | 9/2005 | Boehm, Jr. et al. | |
| 2005/0251138 A1 | 11/2005 | Boris et al. | |
| 2005/0273100 A1 | 12/2005 | Taylor | |

FOREIGN PATENT DOCUMENTS

| | | | |
|---|---|---|---|
| EP | 0 923 355 B1 | 1/2003 | |
| FR | 2783411 A1 * | 3/2000 | A61B 17/7047 |
| FR | 2799116 A1 | 4/2001 | |
| GB | 2 381 755 | 5/2003 | |
| JP | 63 009434 | 1/1988 | |
| JP | 05 103801 | 4/1993 | |
| JP | 08 000638 | 1/1996 | |
| JP | 1998-431345 | 7/1998 | |
| JP | 11-4840 | 1/1999 | |
| JP | 1999-135915 | 1/1999 | |
| JP | 2000-139970 | 5/2000 | |
| JP | 2000-404550 | 5/2000 | |
| JP | 2000-175943 A | 6/2000 | |
| JP | 2000-435680 | 6/2000 | |
| JP | 2001-079024 | 3/2001 | |
| JP | 2001-446158 | 6/2001 | |
| JP | 2001-485243 | 6/2001 | |
| WO | WO 97/09940 | 3/1997 | |
| WO | WO 98/04217 | 2/1998 | |
| WO | WO 99/21501 | 5/1999 | |
| WO | WO 99/38461 | 8/1999 | |
| WO | WO 00/44320 | 8/2000 | |
| WO | WO 2000/66012 A1 | 11/2000 | |
| WO | WO 01/49220 A1 | 7/2001 | |
| WO | WO 03/020141 A1 | 3/2003 | |
| WO | WO 03/020142 A1 | 3/2003 | |

OTHER PUBLICATIONS

Michael F. O'Brien et al., A Novel Technique for Laminoplasty Augmentation of Spinal Canal Area Using Titanium Miniplate Stabilization: A Computerized Morphometric Analysis, Spine, 1996, pp. 474-484, vol. 21 No. 4, Lippincott-Raven Publishers.

Kiyoshi Hirabayashi et al., Operative Procedure and Results of Expansive Open-Door Laminoplasty, Spine, 1988, pp. 870-876, vol. 13 No. 7, Dept. of Orthopaedic Surgery, School of Medicine, Keio Gijuku University, Tokyo, Japan.

Kemal Yucesoy et al., Increase in Spinal Canal Area After Inverse Laminoplasty: An Anatomical Study, Spine, 2000, pp. 2771-2776, vol. 25 No. 21, Lippincott Williams & Wilkins, Inc.

R. Zanasi et al., Open Door Operation to Raise the Vertebral Arch in Myelopathy Due to Cervical Spondylosis, pp. 21-30, Department of Orthopaedics and Traumatology, Fatebenefratelli Hospital, Milan.

J.M. Wang et al., A New Method of Stabilising the Elevated Laminae in Open-Door Laminoplasty Using an Anchor System, The Journal of Bone & Joint Surgery, Nov. 1998, pp. 1005-1008, vol. 80-B No. 6, British Editorial Society of Bone and Joint Surgery.

N. Tsuzuki et al., Tension-band Laminoplasty of the Cervical Spine, International Orthopaedics (SICOT), 1996, pp. 275-284, vol. 20, Springer-Verlag.

Thomas T. Lee et al., Safety and Stability of Open-Door Cervical Expansive Laminoplasty, Journal of Spinal Disorders, 1998, pp. 12-15, vol. 11 No. 1, Lippincott-Raven Publishers, Philadelphia.

Yasuhisa Maezawa et al., Development of Hydrocephalus After Cervical Laminoplasty for Ossification of the Posterior Longitudinal Ligament: Case Report, Spinal Cord, 1996, pp. 699-702, vol. 34, International Medical Society of Paraplegia.

Kiyoshi Hirabayashi et al., Expansive Laminoplasty for Myelopathy in Ossification of the Longitudinal Ligament, Clinical Orthopaedics and Related Research, pp. 35-48, No. 359, Lippincott Williams & Wilkins, Inc., Copyright 1999.

S.S. Praharaj et al., Laminoplasty: An Evaluation of 24 Cases, Neurology India, Sep. 2000, pp. 249-254, vol. 48, Departments of Neurosurgery and Radiology, National Institute of Mental Health and Neurosciences, Banglalore, India.

Thomas T. Lee et al., Modified Open-Door Cervical Expansive Laminoplasty for Spondylotic Myelopathy: Operative Technique, Outcome, and Predictors for Gait Improvement, Neurosurgical Focus, Jan. 23, 2001, 9 pages, http://www.neurosurgery.org/focus/nov96/1-5-p2.html.

Eiji Wada et al., Subtotal Corpectomy Versus Laminoplasty for Multilevel Cervical Spondylotic Myelopathy: A Long-Term Follow-Up Study Over Ten Years, Clinical Award, pp. 155-158.

Maurizio Fornari et al., Artificial Lamina-Assisted Laminoplasty Performed in Seven Cases, J. Neurosurg: Spine, Jul. 1999, pp. 43-49, vol. 91, Departments of Neurosurgery and Neuroradiology, Istituo Nazionale Neurologico "C. Besta", Milan, Italy.

G.R. Gillett et al., CG-Clip Expansive Open-Door Laminoplasty: A Technical Note, British Journal of Neurosurgery, 1999, pp. 405-408,

(56) References Cited

OTHER PUBLICATIONS vol. 13 No. 4, Department of Neurosurgery, Dunedin School of Medicine, University of Otago, New Zealand.
Christopher I. Shaffrey et al., Modified Open-Door Laminoplasty for Treatment of Neurological Deficits in Younger Patients with Congenital Spinal Stenosis: Analysis of Clinical and Radiographic Data, Journal of Neurosurgery, Apr. 1999, vol. 90 No. 2.

* cited by examiner

LAMINOPLASTY DEVICES AND METHODS

CROSS-REFERENCE TO RELATED APPLICATIONS

This application is a continuation of U.S. patent application Ser. No. 12/386,892, which is a divisional of U.S. patent application Ser. No. 10/447,126 filed on May 28, 2003, which claims the benefit of the filing date of the Provisional Application Ser. No. 60/384,573 filed May 30, 2002. Each of the referenced applications is incorporated herein by reference in its entirety.

BACKGROUND

The present invention relates to the field of laminoplasty, and, more particularly, to laminoplasty devices and methods.

Every year there are a significant number of people who suffer severe neck, back, and/or spine injuries from trauma (see FIG. 1 for a perspective view of a typical human spine 100, including the cervical 110, thoracic 120, lumbar 130, sacrum 140, and coccyx 150 regions). These injuries include cervical fractures, fracture dislocations combined with retropulsion of the disc, and other major injuries. Also, each year many people undergo spine surgery for degenerative diseases, especially degenerative spinal stenosis. In spinal stenosis, the spinal canal, which contains and protects the spinal cord and nerve roots, narrows, which results in compression of the spinal cord and nerves. Surgical goals can include a decompression of all compressed levels of the spine and stabilization with solid fusion.

To provide further anatomical background, FIG. 2 is a perspective view, showing the structure of a typical vertebra 200. The exact structure of the vertebrae in each section of the spine may vary somewhat to accommodate the function required of that section. Nevertheless, the typical vertebra 200 includes an anterior portion called the spinal body 210 and a posterior portion called the vertebral arch 220 which surround the spinal canal 280. The vertebral arch 220 includes the spinous process 250, which is connected to the articular facet 230 and the transverse facet 260 by laminae 240. The facets 230, 260 are connected to the spinal body 210 by pedicles 270.

There are two posterior surgical methods for creating more room in the spinal canal. The first is a laminectomy in which the bony structures forming the back of the canal and the associated ligaments are removed. In the cervical region, a laminectomy can lead to spinal instability, or what is referred to as the "swan neck" deformity. This deformity can be a very difficult problem to correct and can cause substantial discomfort in the neck and shoulders due to the lack of the supporting structures at the back of the vertebrae which normally perform some of the work of keeping the neck in the right shape. It can also lead to further spinal cord damage.

An alternative way of relieving spinal cord pressure is a surgical procedure called a laminoplasty. Laminoplasty procedures concern altering one or more of the bony vertebral structures that surround and define the spinal canal. For example, the bony structures can been weakened and flexed or swung posteriorly to open the canal and provide additional room for the spinal cord. A problem associated with this procedure concerns stabilizing the altered one or more vertebrae for proper healing.

The laminoplasty technique is often referred to as an "open door laminoplasty," because the back of one or more vertebrae is made to swing open like a door. There are multiple variations of the laminoplasty procedure, including the hemilateral open door laminoplasty (a.k.a., single door laminoplasty), and the bilateral open door laminoplasty (a.k.a., middorsal laminoplasty, French door laminoplasty, or double door laminoplasty).

For the hemilateral open door laminoplasty, one challenge is to securely maintain the separation between the posterior portion and the anterior portion of the divided lamina. Although it is known to use a bone graft to provide this separation, the use of such grafts can require additional surgery and time to harvest an appropriate piece of graft bone, typically from the pelvis of the patient or cadaver. Moreover, it is possible for the bone graft to move after the laminoplasty surgery. This potentially causes a narrowing of the cross-sectional area of the spinal canal, impingement on the patient's spinal cord, and/or disruption or prolongation of fusion.

With regard to the French door laminoplasty, the challenges can be even greater. For example, sutures have been used to secure a bone graft to the sectioned and separated laminae. Such sutures, however, are technically difficult, time consuming to insert, and typically do not firmly secure the bone graft to the sectioned laminae. Thus, subsequent movement between the bone graft and either of the two sectioned laminae can disadvantageously disrupt and/or prolong fusion therebetween.

SUMMARY

A laminoplasty plate is provided for use with a spinal canal having an increased cross-sectional area. The plate includes a spacer portion that spans a gap formed by displacement of divided lamina portions. The plate includes a first lamina engagement portion adjacent a first end of the bone spacer portion that includes a first plurality of flanges. The first flanges are positionable in contact with or adjacent to an outer surface of the first divided spinal lamina at one or more locations about the lamina.

A laminoplasty plate is provided to stabilize a surgically divided spinal lamina associated with a laminoplasty. The plate includes a spacer portion and a lamina engagement portion. The lamina engagement portion can include a cup, a cuff, and/or a plurality of flanges for receiving or extending about a portion of the divided lamina.

A laminoplasty plate is provided for stabilizing at least one surgically divided spinal lamina associated with a laminoplasty. The plate includes a spacer portion spanning a gap formed by a removal of a spinal process and a separated pair of laminae. The plate also includes a first lamina engagement portion adjacent a first end of the spacer portion, the first lamina engagement portion including a first bone-grasping portion. The plate further includes a second lamina engagement portion adjacent a second end of the spacer portion, the second lamina engagement portion including a second bone-grasping portion.

A laminoplasty plate is provided for securing a surgically divided spinal lamina associated with a laminoplasty. The plate includes a spacer portion for spanning a gap formed by removal of at least a portion of a lamina during the laminoplasty. The plate also includes a first engaging portion adjacent a first end of the spacer portion. The first engaging portion extends along at least first and second sides of the divided spinal lamina.

There is provided a plate for a laminoplasty procedure that includes increasing a cross-sectional area of a spinal canal. The plate comprises a spacer portion having a first end and a second end. The spacer portion is positionable between first and second portions of a divided spinal lamina. The plate includes a first lamina engagement portion adjacent the first end of the spacer portion. The first lamina engagement portion includes a first plurality of lamina stabilizing flanges extendable along at least two of the anterior, posterior, superior and inferior surfaces of the first portion of the divided lamina.

There is provided a plate for a laminoplasty procedure that increases a cross-sectional area of a spinal canal. The plate comprises a spacer portion having a first end and a second end. The spacer portion is positionable between first and second portions of a divided spinal lamina. The plate includes a first lamina engagement portion adjacent the first end of the spacer portion. The first lamina engagement portion includes a first plurality of flanges positionable along at least two of the anterior, posterior, superior and inferior surfaces of the first portion of the divided lamina. A second lamina engagement portion can be provided adjacent the second end of the spacer portion. The second lamina engagement portion can include one or more flanges positionable along at one of the anterior, posterior, superior and inferior surfaces of the second portion of the divided lamina.

There is provided a plate for stabilizing a surgically divided spinal lamina associated with a laminoplasty that includes a spacer portion positionable between the spinal lamina and at least one lamina engagement portion. The lamina engagement portion includes at least one flange having a bone engagement mechanism extending therefrom for engaging the adjacent portion of the divided lamina.

There is provided a laminoplasty plate for stabilizing a surgically divided spinal lamina associated with a laminoplasty. The plate comprises a spacer portion and a plurality of flanges extending therefrom for restraining movement between the spacer portion and the surgically divided spinal lamina in at least two directions.

There is provided a plate for a laminoplasty procedure that increases a cross-sectional area of a spinal canal. The plate comprises a spacer portion positionable in a gap formed by displacement of a first divided spinal lamina portion. A first lamina engagement portion extending from an end of the spacer portion is adapted to contact the first divided spinal lamina portion at a plurality of locations about its perimeter.

There is provided a laminoplasty plate for securing a surgically divided spinal lamina associated with a laminoplasty. The plate comprises a spacer portion having a first end and a second end. The spacer portion is positionable in or adjacent a gap formed by removal of at least a portion of a lamina during the laminoplasty. The plate includes a first lamina engagement portion extending from the first end of the spacer portion. The lamina engagement portion includes one of a lamina engaging cup or cuff adapted to extend substantially about a first portion of the divided spinal lamina.

There is provided a laminoplasty plate for stabilizing a surgically divided spinal lamina associated with a laminoplasty that includes a spacer portion and a lamina engaging cup adjacent an end of the spacer portion.

There is provided a laminoplasty plate for stabilizing a surgically divided spinal lamina associated with a laminoplasty that includes a spacer portion and a lamina engaging cuff adjacent an end of the spacer portion.

There is provided a laminoplasty plate for stabilizing a surgically divided lamina associated with a laminoplasty. The plate includes a spacer portion having opposed first and second ends. The spacer portion is positionable in or adjacent a gap formed by a removal of a spinal process and/or separated portions of one or more lamina. Adjacent one end of the spacer portion is a first lamina engagement portion that includes a first bone-grasping portion. A second lamina engagement portion is adjacent the other end of the spacer portion and includes a second bone grasping portion.

A method for stabilizing at least one surgically divided spinal lamina associated with a laminoplasty is provided. The method includes providing a laminoplasty plate having a spacer portion that includes a first end and a second end, the laminoplasty plate also having a first lamina engagement portion adjacent the first end, the first lamina engagement portion including a first plurality of bone grasping portions. The method also includes retaining a predetermined gap between a first divided lamina portion and a second divided lamina portion with the spacer portion of the laminoplasty plate.

There is provided a method for stabilizing a surgically divided spinal lamina associated with a hemilateral open door laminoplasty. The method includes providing to a surgical patient a laminoplasty plate having a spacer portion that includes a first end and a second end, the laminoplasty plate also having a first engagement portion adjacent the first end of the spacer portion. The method further includes contacting the first engagement portion to an anterior surface and a posterior surface of a first portion of a divided spinal lamina.

There is provided a method for stabilizing surgically divided spinal laminae associated with a French door laminoplasty that includes providing to a surgical patient a laminoplasty plate having a spacer portion that includes opposed first and second ends. The laminoplasty plate also has a first lamina engagement portion adjacent the first end of the spacer portion and a second lamina engagement portion adjacent the second end of the spacer portion. The plate is positioned adjacent the divided spinal laminae so that the plate extends between a first divided lamina and a second divided lamina and across a gap formed by a removal of a spinal process associated with the vertebra.

BRIEF DESCRIPTION OF THE DRAWINGS

The invention and its wide variety of potential embodiments will be more readily understood through the following detailed description, with reference to the accompanying drawings in which.

DETAILED DESCRIPTION

Figure 1:
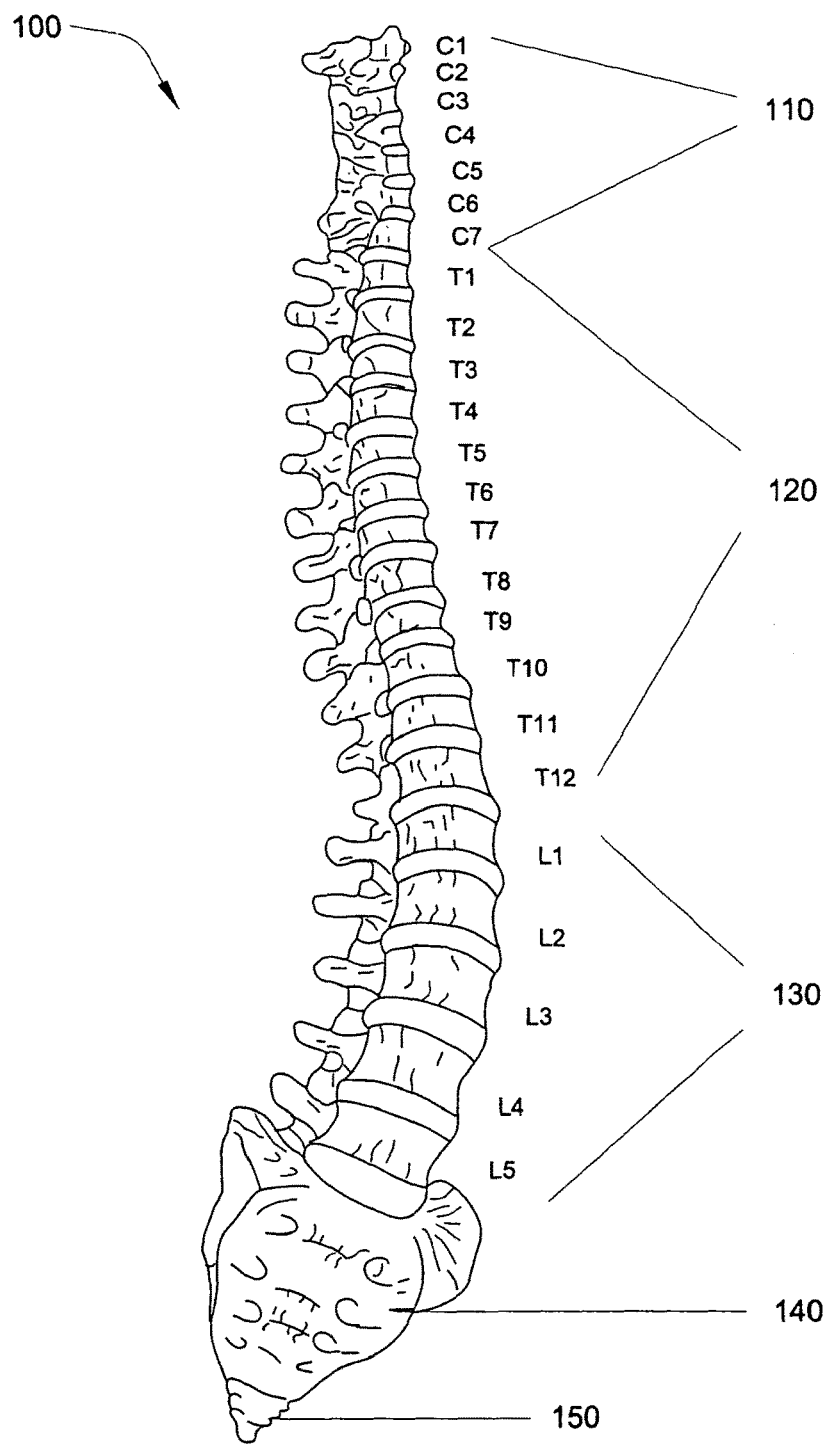
FIG. 1 is a perspective view of a typical human spine.
Figure 2:
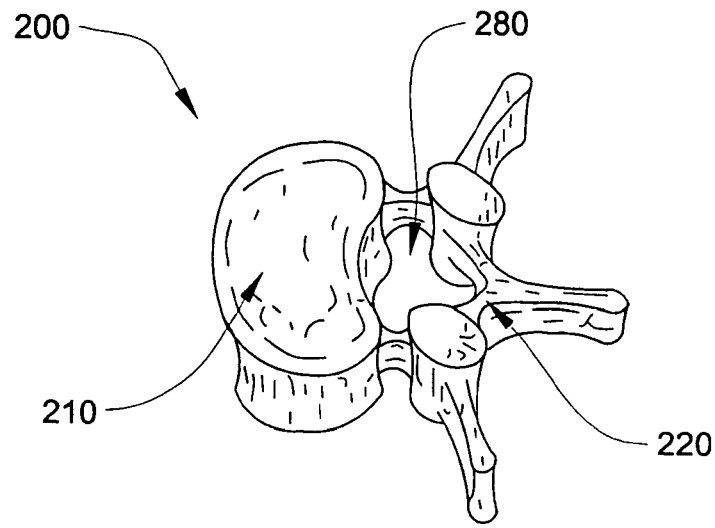
FIG. 2 is a perspective view of a typical vertebra.
Figure 3:
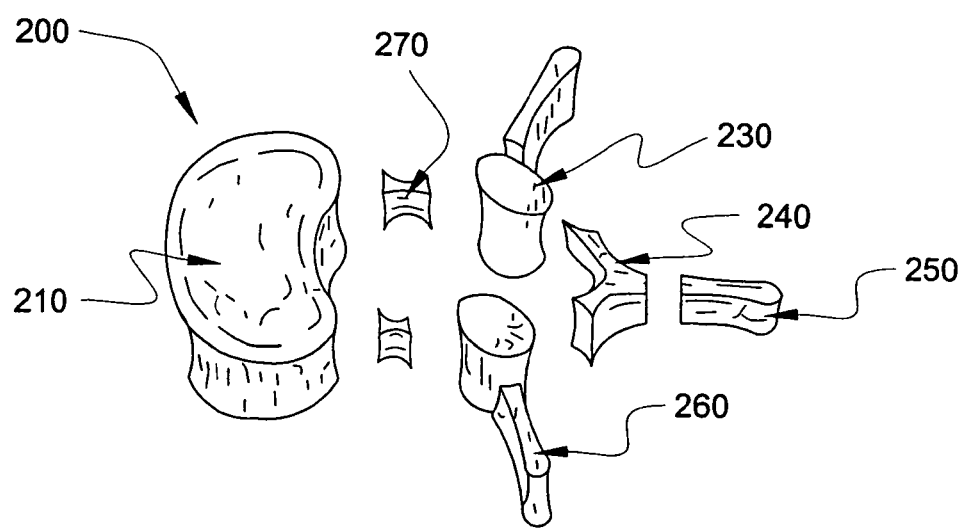
FIG. 3 is an exploded perspective view of the typical vertebra of FIG. 2.
Figure 4:
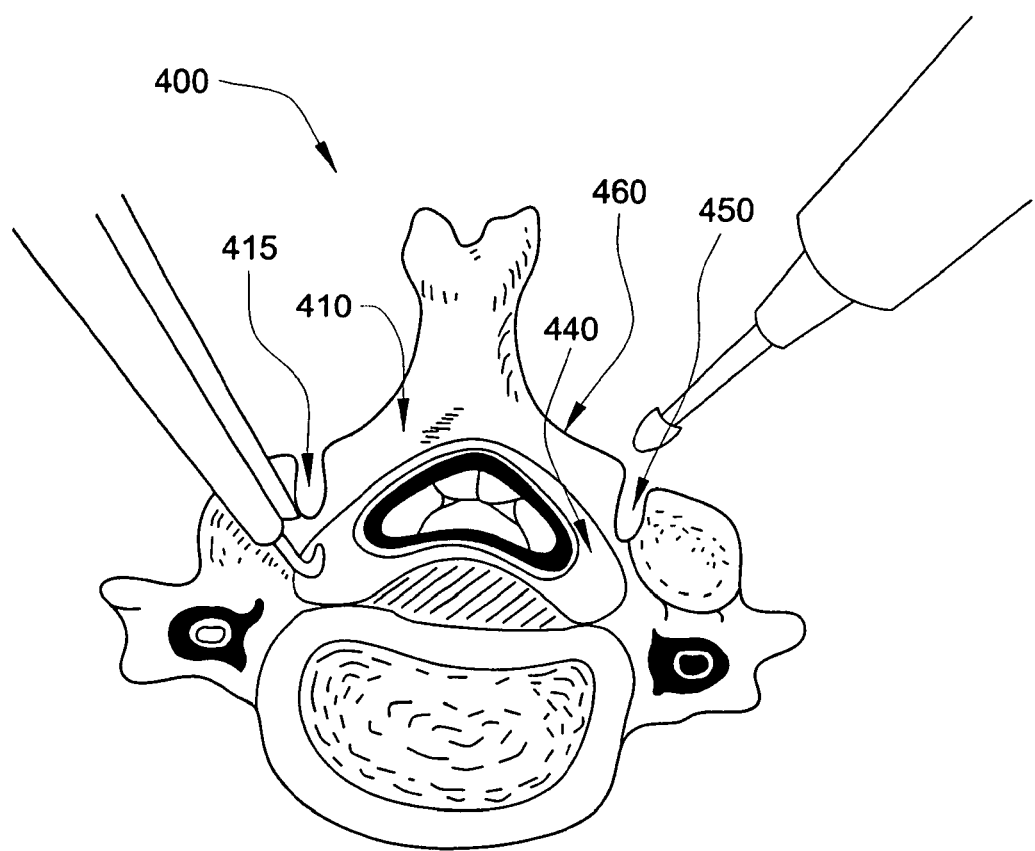
FIG. 4 is a plan view of a first stage of a hemilateral open door laminoplasty.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

A system for stabilizing first and second divided lamina portions as a result of a laminoplasty procedure is provided. The divided lamina portions can be created as the result of hemilateral open door laminoplasty or French door laminoplasty procedures. Certain embodiments may be more particularly suited for a certain laminoplasty procedure, however, aspects of each embodiment have application in any laminoplasty procedure.

FIGS. 4-7 are plan views showing a procedure for a hemilateral open door laminoplasty on vertebra 400 for securement of a laminoplasty system 700. In the initial stage of the procedure the patient is positioned appropriately, and an incision is made to expose the posterior elements of the vertebrae of interest. Typically, any osteophytes are removed, and the spinous process can be removed. A relief 415 is cut down the medial cortical layer of lamina 460 of at least one vertebra 400. Relief 415 can be in the form of a groove, gutter, or trough, and formed using a high-speed burr drill. In one specific embodiment, relief 415 has a depth of approximately 3 to 4 millimeters and a width of approximately 3 millimeters to divide the lamina on what will be the "open" side. Then, a similar method can be used to thin the bone of lamina 460 on the opposite side to create a bone hinge 450. In addition, the associated ligamentum flavum, capsule, and/or veins can be divided to allow outward rotation of the divided lamina.

Figure 5:
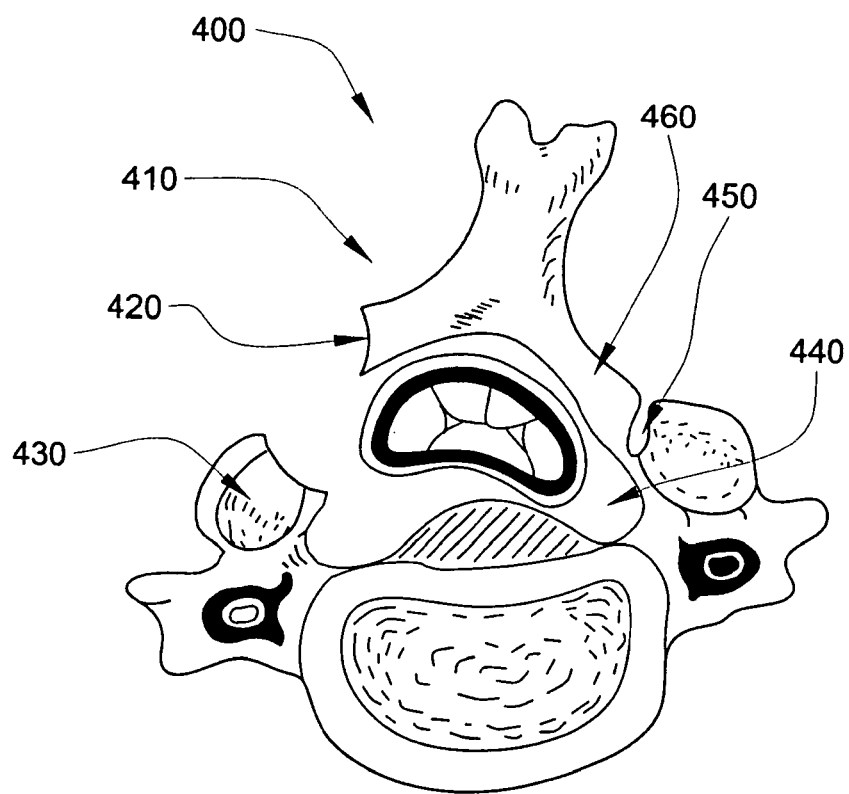
FIG. 5 is a plan view of a second stage of a hemilateral open door laminoplasty.
Figure 6:
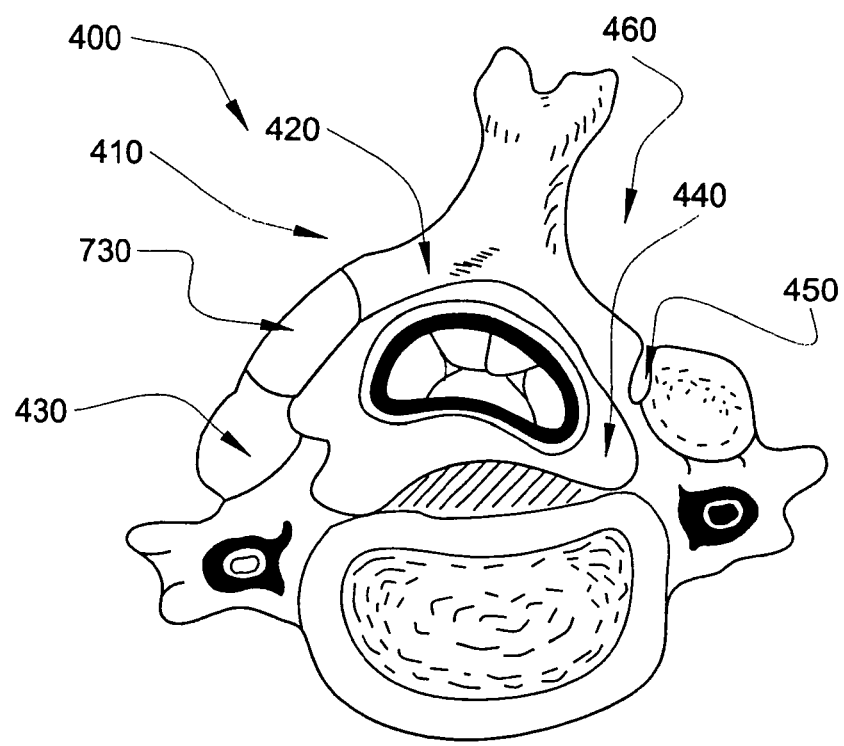
FIG. 6 is a plan view of a third stage of a hemilateral open door laminoplasty showing a bone graft inserted between the divided lamina portions.

In FIG. 5 the posterior portion 420 of the divided lamina 410 is rotated outwardly or posteriorly about the hinged lamina 460, thereby opening and enlarging the cross-sectional area of the spinal canal 440. In FIG. 6, spacer member 730 is inserted between the posterior portion 420 of the divided lamina and the anterior portion (lateral mass) 430 of the divided lamina. Spacer member 730 can prevent posterior portion 420 of the divided lamina from closing from the new position toward the original position. The divided lamina can tightly abut spacer member 730, which can act as a wedge to prevent further movement of the divided lamina toward one another.

The spacer members discussed herein can be a non-fusion member that supports the divided lamina, or a fusion member that also provides an avenue or platform for fusion of the divided lamina. For example, the spacer members can be a bone graft or an artificial device providing one or more avenues for bone growth between the divided lamina. The spacer members can be constructed of any biocompatible material, including metals and metal alloys, ceramics, plastics, resorbable materials, non-resorbable materials, bone material and/or composites. The spacer members can be a bone graft made from actual or synthetic bone and/or DBM (demineralized bone matrix). The spacer members can include a bone growth facilitating or inducing material, such as a bone chips, paste or putty and/or carriers such as a sponge, matrix, and/or sheet impregnated with a protein such as BMP (bone morphogenic protein), LMP (LIM Mineralization Protein), etc.

Figure 7:
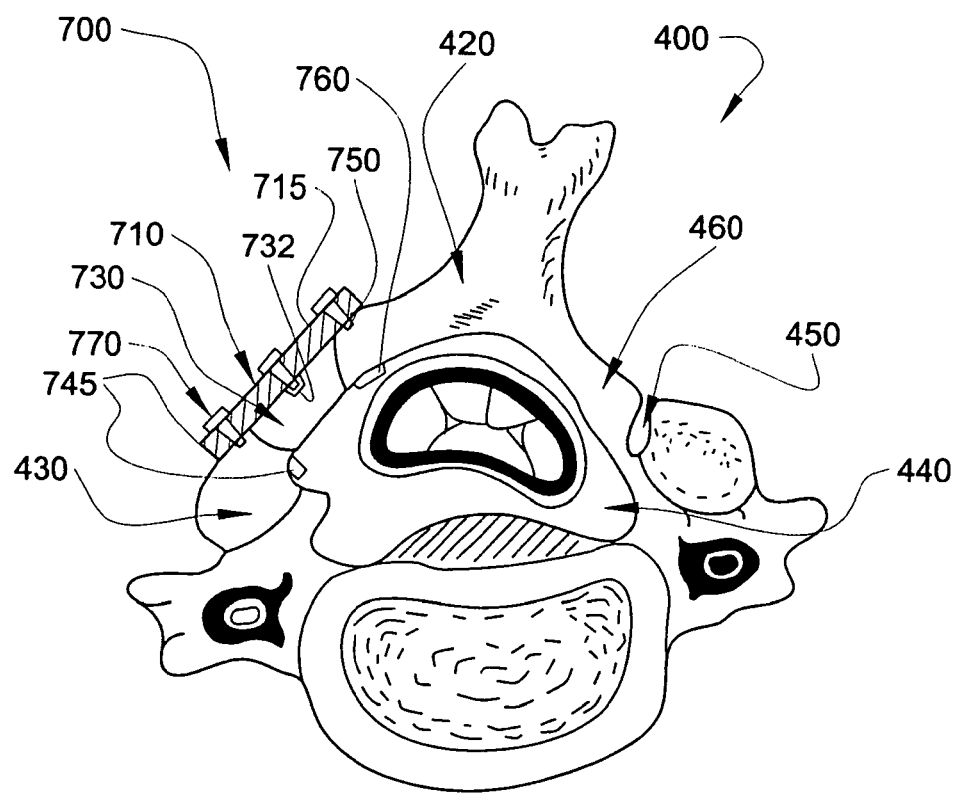
FIG. 7 is a plan view in partial section of a fourth stage of a hemilateral open door laminoplasty and one embodiment of a laminoplasty plate of the present invention.

FIG. 7 includes laminoplasty system 700 for stabilizing first and second divided lamina portions separated to enlarge the spinal canal. System 700 includes a laminoplasty plate 710 secured to one or more vertebra upon which a hemilateral open door laminoplasty has been performed. Laminoplasty plate 710 can be attached to the posterior portion 420 of the divided lamina, optionally to a spacer member 730, and to the anterior portion (lateral mass) 430 of the divided lamina (and/or to the articular facet) to secure the spacer member 730 in place. Laminoplasty plate 710 resists the door or opening between the divided lamina from opening or closing, and also maintains the positioning of spacer member 730.

Laminoplasty plate 710 can include a spacer portion 715 and a lamina engaging portion at one end thereof including a first plurality of flanges 750, 760. The lamina engaging portion is engageable with the adjacent posterior portion 420 of the lamina to assist in reducing, restraining, and/or preventing the movement of the posterior portion 420 relative to plate 710 and/or with respect to the spacer member 730. This can promote healing by, for example, facilitating fusion between the end of the posterior portion 420 and the end of the spacer member 730.

The opposite end of central spacer portion 715 includes a second lamina engaging portion. In the illustrated embodiment, the second lamina engaging portion includes one or more flanges 745 that assist in reducing, restraining, and/or preventing the movement of the anterior portion 430 of the divided lamina and/or lateral mass relative to plate 710 and/or with respect to spacer member 730. This can promote healing by, for example, facilitating fusion between the divided end of the anterior portion 430 and the end of spacer member 730. Spacer portion 715 can have sufficient structural strength to shield the spine and/or spinal canal in a manner approximately equivalent to, and/or better than, the pre-surgery bone structure.

One or more securement mechanisms 770, such as a screw with or without a locking mechanism, can be inserted through laminoplasty plate 710 via one or more securement openings through the plate 710 and into divided lamina portions 420, 430, and/or spacer member 730. Spacer member 730 may further include one or more drilled and/or threaded bores 732 for receiving and engaging one or more securement mechanisms 770 inserted through laminoplasty plate 710, thereby securing laminoplasty plate 710 to spacer member 730. Securement mechanisms other than bone screws are also contemplated, such as fasteners, anchors, nails, staples, nuts and bolts, glue, bone cement, and/or pins.

Figure 8:
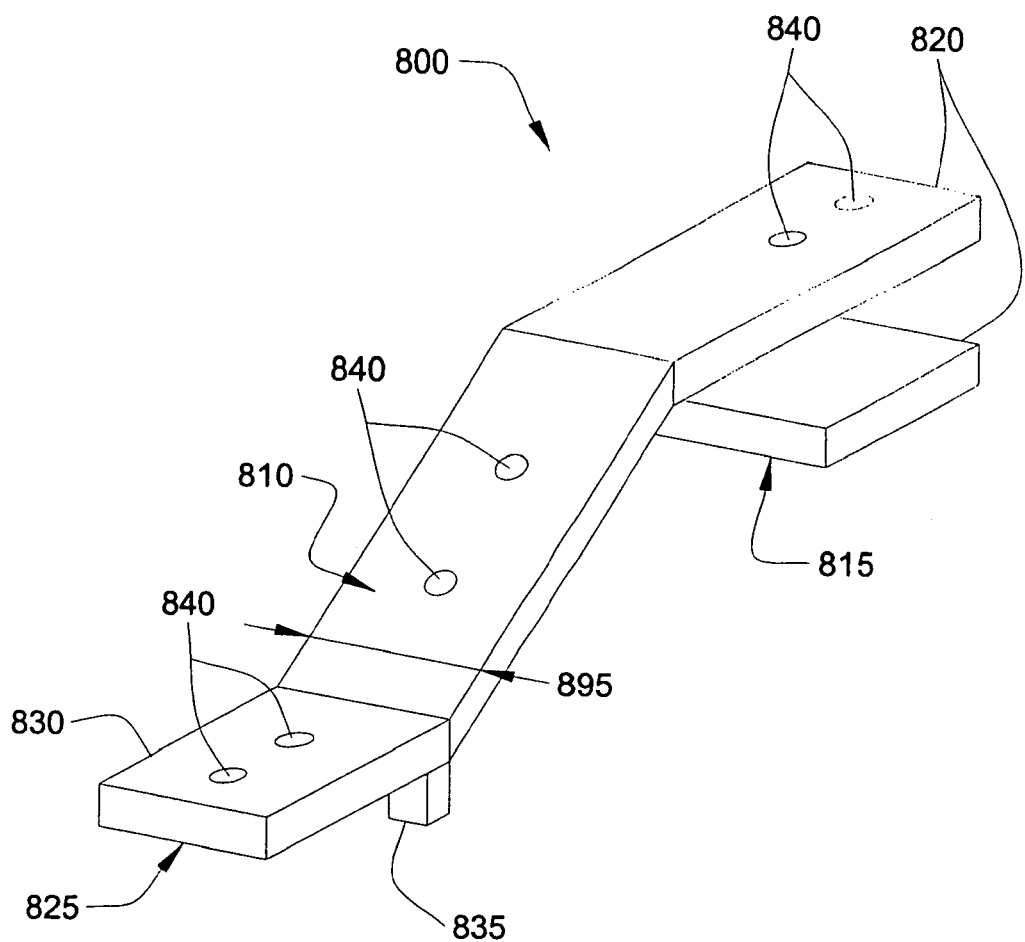
FIG. 8 is a perspective view of another embodiment laminoplasty plate.
Figure 9:
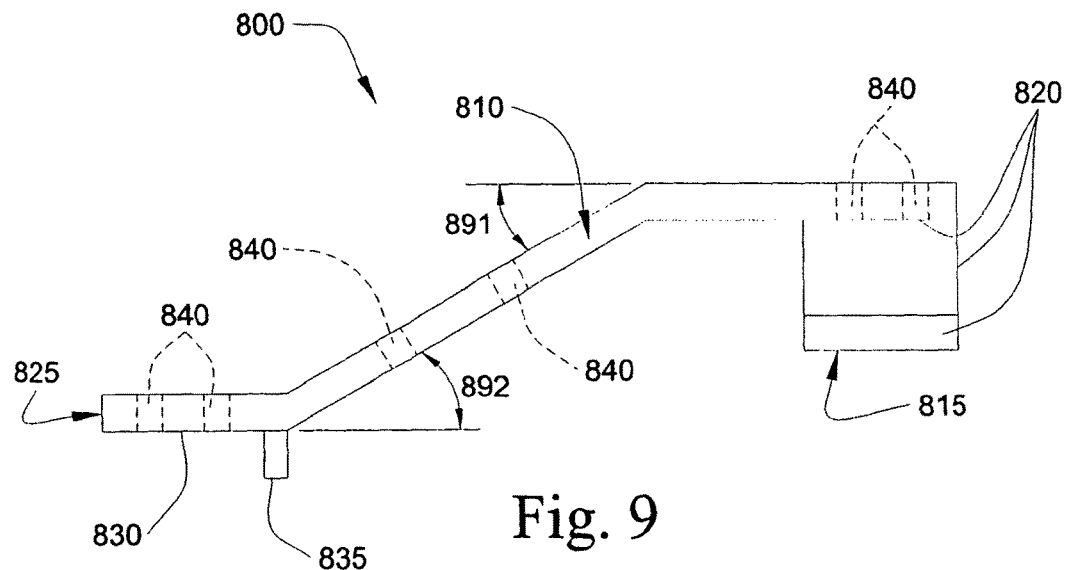
FIG. 9 is an elevation view of the laminoplasty plate of FIG. 8.
Figure 10:
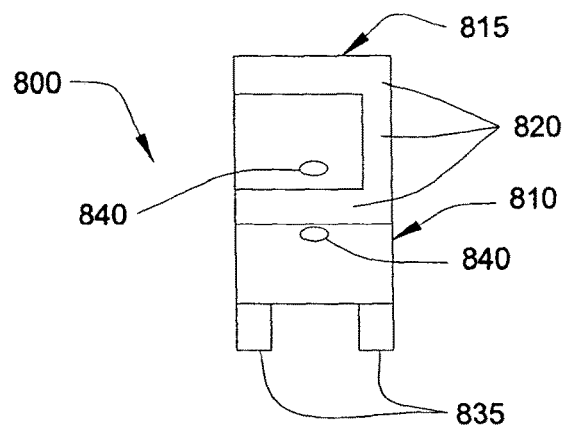
FIG. 10 is a right side view of the laminoplasty plate of FIG. 8.

FIGS. 8, 9 and 10 show another embodiment laminoplasty plate 800 that can be employed, for example, with a hemilateral open door laminoplasty system, although application with other laminoplasty procedures is contemplated. Plate 800 includes a spacer portion 810 sized to span the divided portions of the lamina when in their appropriate respective open door positions. One end of spacer portion 810 includes a first lamina engaging portion 815 that includes a first plurality of flanges 820 that can be attached to or engage adjacent, opposing, and/or distributed locations about exterior surfaces of, for example, the posterior portion of the divided lamina.

The other end of spacer portion 810 includes a lamina engaging portion 825 that includes a second plurality of flanges 830, 835 that can be attached to or engage adjacent, opposing, and/or distributed locations on an exterior surface of, for example, an anterior portion of the divided lamina and/or the corresponding facet. Flange 830 can extend along the posterior surface of the anterior portion of the divided lamina. Flanges 835 can each be a ledge that abuts and/or engages the divided surface of the anterior portion of the divided lamina, i.e. the surface oriented toward the other divided lamina portion. Flanges 835 are positioned adjacent respective ones of the superior and inferior edges of spacer portion 810, and flange 830 extends from and has generally the same width as spacer portion 810. The space between flanges 835 provides a pathway for engagement of the spacer member with a bony surface of the divided lamina portion. Flanges 835 can be transverse to flange 830. In one embodiment, flanges 835 are orthogonal to flange 830. Other embodiments contemplate other orientations between flanges 835 and flange 830.

Securement openings 840 can receive a securement mechanism such as, for example, a screw to be inserted into the underlying bone and/or fusion member (not shown) and secure the laminoplasty plate to the bone and/or fusion member. The securement mechanisms can include a locking mechanism, such as tabs or a secondary screw, to prevent backing out from the openings 840. Spacer portion 810 can be provided with a width 895 extending in the direction of the central spinal column axis when plate 800 is secured to the divided lamina. In one specific embodiment, width 895 can be sized for a single vertebral level, and can range from about 5 millimeters to about 20 millimeters. Other embodiments contemplate other values for width of the spacer portions discussed herein. For example, the widths can be sized to span two or more vertebral levels.

Flange 820 forms an angle 891 with spacer portion 810, and flange 830 along the posterior face of the divided lamina portion forms an angle 892 with spacer portion 810. Angles 891 and 892 can be the same, as shown, or be of different values. In one specific embodiment, angles 891 and 892 can be about 45 degrees. Other embodiments contemplate angles 891 and 892 ranging from 35 to 55 degrees, ranging from 25 to 65 degrees, or ranging from 0 degrees to 90 degrees.

Figure 11:
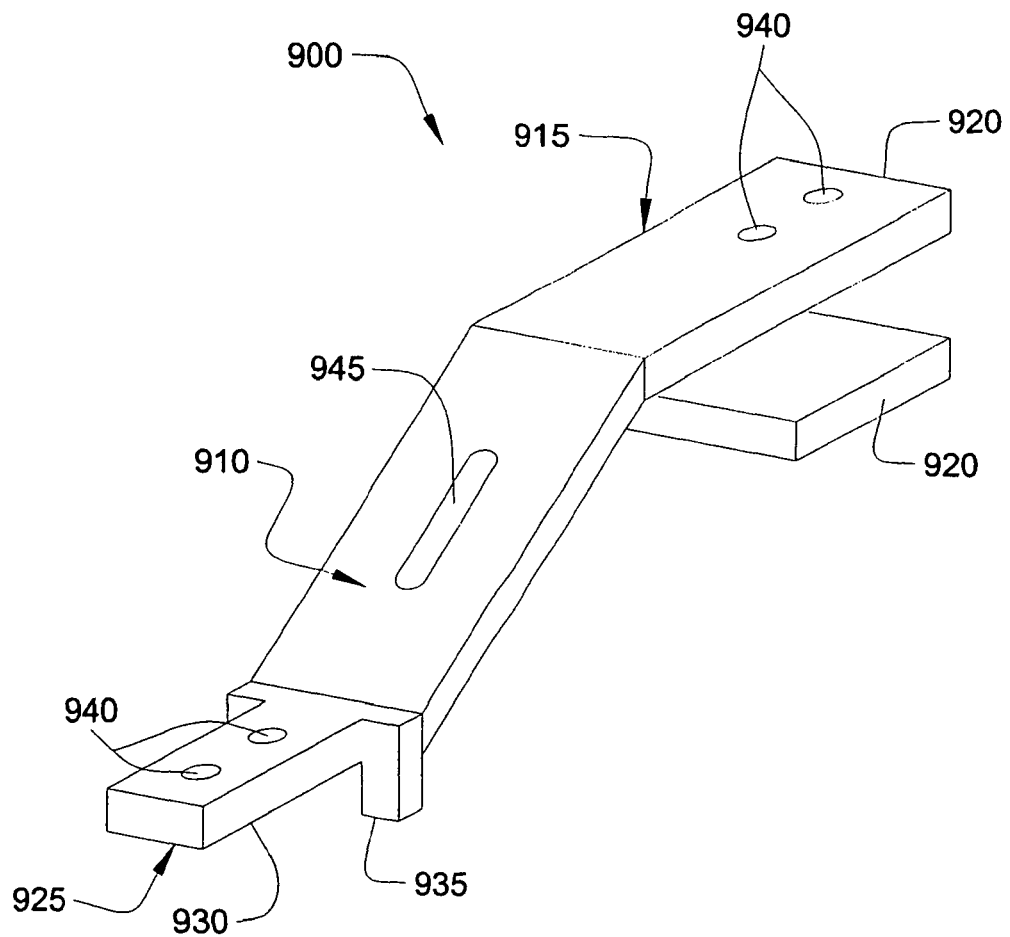
FIG. 11 is a perspective view another embodiment laminoplasty plate
Figure 12:
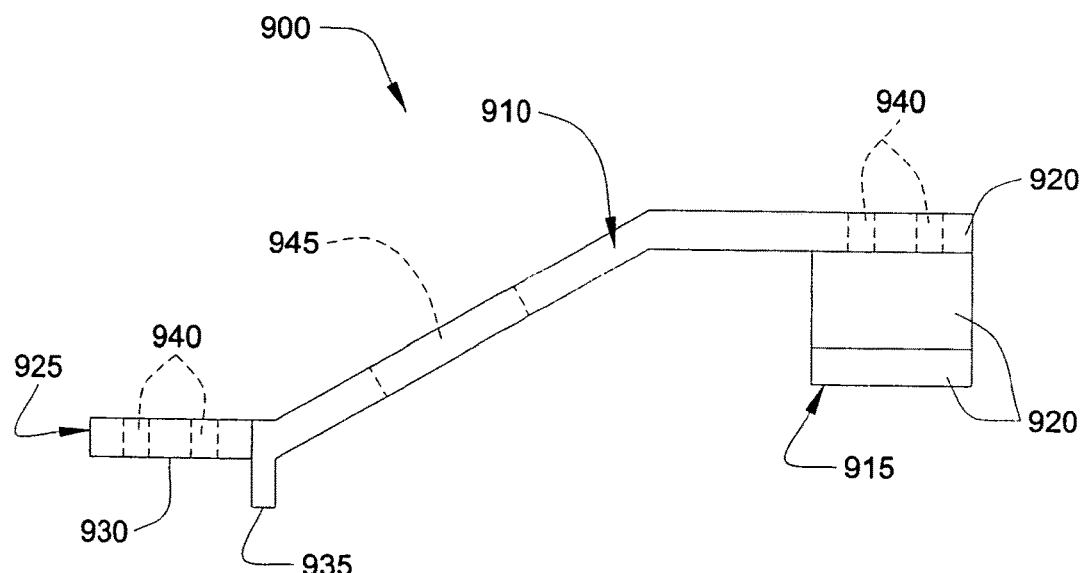
FIG. 12 is an elevation view of the laminoplasty plate of FIG. 11.
Figure 13:
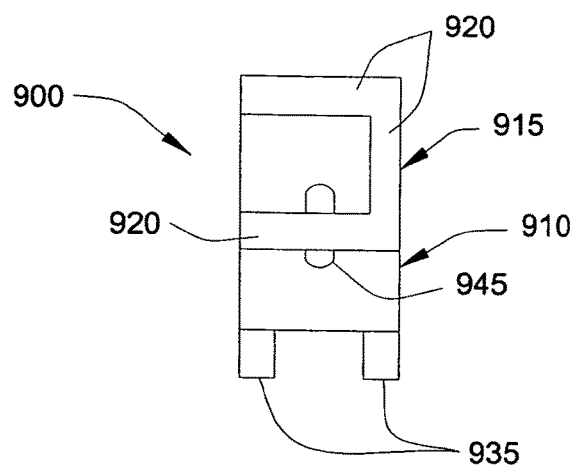
FIG. 13 is a right side view of the laminoplasty plate of FIG. 11.

FIGS. 11, 12 and 13 show another embodiment laminoplasty plate 900 that can be that can be employed, for example, with a hemilateral open door laminoplasty system, although application with other laminoplasty procedures is contemplated. Except as noted, laminoplasty plate 900 can be similar to laminoplasty plate 800 of FIGS. 8, 9 and 10. One end of a spacer portion 910 includes a first lamina engaging portion 915 that includes a first plurality of flanges 920 that can be attached to or engage adjacent, opposing, and/or distributed locations about exterior surfaces of, for example, the posterior portion of the divided lamina.

Plate 900 includes a second lamina engaging portion 925 at the other end of spacer portion 910 that includes flange 930 and a pair of flange ledges 935. Flange ledges 935 are positioned adjacent to one of the edges of spacer portion 910, and flange 930 extends from spacer portion 910 between flanges 935. Flanges 935 can be transverse to flange 930. In one embodiment, flanges 935 are orthogonal to flange 930. Other embodiments contemplate other orientations between flanges 935 and flange 930. Securement openings 940 can allow one or more securement mechanisms (not shown) such as, for example a bone screw, to be inserted into the underlying bone and/or a spacer member (not shown) and secure laminoplasty plate 900 to the underlying lamina portion. A slotted securement opening 945 in spacer portion 910 can be provided to permit variable orientation and placement of one or more securement mechanisms relative to the underlying spacer member. Slotted securement opening 945 allows infinitely variable placement of the fastener therealong. Other embodiments contemplated slotted securement opening 945 with recesses forming one or more discrete fastener locations therealong.

Figure 14:
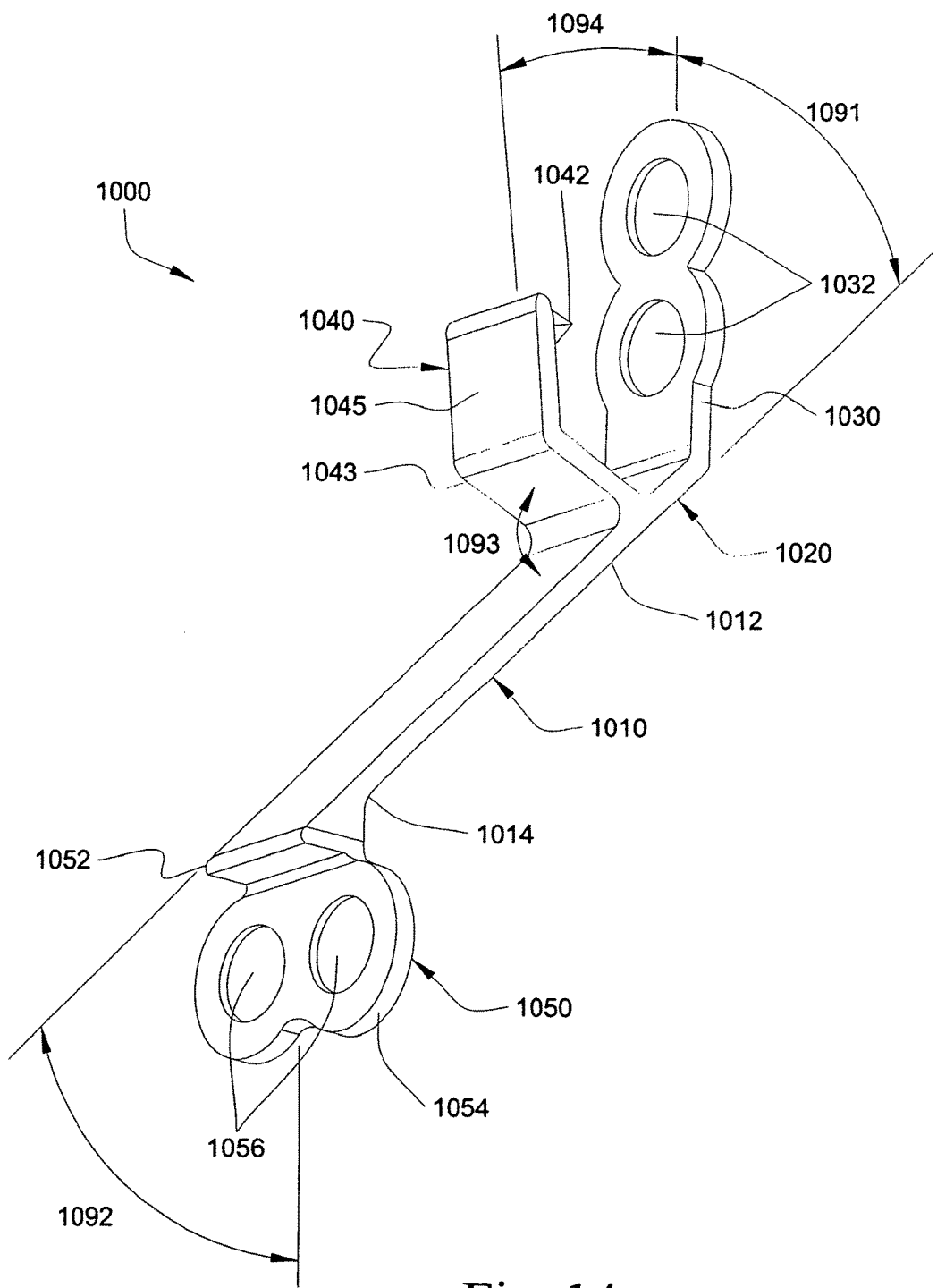
FIG. 14 is a perspective view of a further embodiment laminoplasty plate.

FIG. 14 is a perspective view of another embodiment laminoplasty plate 1000 that can be employed, for example, with a hemilateral open door laminoplasty system, although application with other laminoplasty procedures is contemplated. Plate 1000 can include a spacer portion 1010 having a first end 1012 and a second end 1014. The longitudinal length of spacer portion 1010 can correspond to a desired separation distance between a posterior portion and an anterior portion of a divided lamina.

Adjacent first end 1012 is a first engaging portion 1020 which can serve to reduce and/or prevent movement of a first divided lamina portion with respect to laminoplasty plate 1000 in at least two directions. First engaging portion 1020 can include one or more lamina stabilizing flanges, such as first lamina stabilizing flange 1030 and second lamina stabilizing flange 1040. To reduce, restrain, and/or prevent movement of the lamina portion with respect to laminoplasty plate 1000, any flange 1030, 1040 can be positioned and/or distributed about an expected longitudinal axis of the lamina portion, and/or can be of a sufficient length to at least partially capture or receive the lamina portion therebetween. Moreover, any flange 1030, 1040 can be of sufficient length to include one or more securement openings 1032. Further, to grasp, grip, engage, crimp, clamp, capture, and/or restrain bone, any flange 1030, 1040 can include a bone engagement mechanism 1042. In the illustrated embodiment, bone engagement mechanism 1042 includes an elongated, pointed ridge that can bite into the adjacent bone. Other bone engagement mechanisms are contemplated, including one or more teeth, ridges and valleys, ledges, spikes, knurlings, friction increasing feature, and/or bone bearing surface, for example.

First flange 1030 of first engaging portion 1020 can form an angle 1091 with respect to spacer portion 1010, which can approximately range in one embodiment from 5 to 85 degrees. In another embodiment, the angle 1091 between first flange 1030 and spacer portion 1010 is in the range of 15 to 75 degrees. In another embodiment, the angle 1091 between first flange 1030 and spacer portion 1010 is in the range of 30 to 60 degrees. In still another embodiment, the angle 1091 between first flange 1030 and spacer portion 1010 is in the range of 40 to 50 degrees.

First flange 1030 can contact a posterior surface of the posterior portion of the divided lamina. Likewise, second flange 1040, positioned medially of first flange 1030, can contact an anterior surface of the posterior portion of the divided lamina. Second flange 1040 is shown extending transversely from and then longitudinally along spacer portion 1010. Second flange 1040 can extend in any direction from spacer portion 1010, or can extend from first flange 1030. First and second flanges 1030, 1040 form a receptacle to contain a divided lamina portion and restrict its relative movement with respect to plate 1000 in at least two directions.

Second flange 1040 includes a connecting portion 1043 that forms angle 1093 with spacer portion 1010, and an end portion 1045 that extends away from first flange 1030 at an angle 1094. In one specific embodiment, angle 1093 is about 67 degrees and angle 1094 is about 8 degrees. Other embodiments contemplate angles 1093 ranging from 45 degrees to 90 degrees, ranging from 25 degrees to 135 degrees, or ranging from 10 degrees to less than 180 degrees. Other embodiments contemplate angle 1094 ranging from 15 degrees to 0 degrees, or ranging from 45 degrees to 0 degrees. It is also contemplated that the end portion 1045 can converge toward first flange 1030.

The pair of flanges 1030, 1040 can cooperate to engage with the posterior portion of the divided lamina. In one embodiment, flanges 1030, 1040 can be bent, deformed, or moved toward one another to clamp, secure, and/or stabilize the posterior portion of the divided lamina. If a securement mechanism extending through securement openings 1032 were to pull loose, disengage, and/or detach from the posterior portion of the divided lamina, the laminoplasty plate could remain engaged to the posterior portion of the divided lamina by engagement of flanges 1030, 1040 with the divided lamina portion.

Second end 1014 of spacer portion 1010 include a second engaging portion 1050 having a first flange 1052 and a second flange 1054 with one or more securement holes 1056. First flange 1052 can be a bone ledge that is configured to provide a surface that faces and opposes an end surface of a dissected bone, such as the anterior portion (lateral mass) of the divided lamina. First flange 1052 can be planar, flat, curved, curvilinear, undulating, contiguous, and/or discontiguous to conform to the profile of the bone against which it is positioned. Second flange 1054 of second engaging portion 1050 can form an angle 1092 with respect to spacer portion 1010, which can range in one embodiment from 5 to 85 degrees. In another embodiment, angle 1092 between second flange 1054 and spacer portion 1010 is in the range of 15 to 75 degrees. In another embodiment, angle 1092 between second flange 1054 and spacer portion 1010 is in the range of 30 to 60 degrees. In still another embodiment, angle 1092 between second flange 1054 and spacer portion 1010 is in the range of 40 to 50 degrees.

Although not shown, first flange 1052 and/or second flange 1054 can include one or more additional bone engagement mechanism to grasp, grip, engage, crimp, clamp, capture, and/or restrain the adjacent bone of the divided lamina portion. Examples of such engagement mechanisms include at least one bone engagement tooth, notch, rib, groove, thread, spline, spike, knurling, ridge, valley, ledge, friction increasing feature, and/or bone bearing surface.

Second engaging portion 1050 of laminoplasty plate 1000 can be attached to, for example, the anterior portion of the divided lamina (and/or the facet) via one or more securement mechanisms that extend through securement holes 1056. Even if these securement mechanisms loosen, first flange 1052 and/or second flange 1054 can resist second engaging portion 1050 of laminoplasty plate 1000 and the anterior portion of the divided lamina from moving into the spinal canal or impinging upon the spinal cord. Moreover, first flange 1052 can cooperate with the pair of flanges 1030, 1040 and spacer portion 1010 to abut the divided ends of the lamina to prevent the divided lamina from moving into the "closed door" position. The lamina engaging portions 1020 and 1050 also abut or engage the posterior surface of the divided lamina to resist the plate from drifting into the spinal canal and reducing the newly expanded cross-sectional area.

Second flange 1040 is shown extending tranversely from spacer portion 1010 and then generally parallel to first flange 1030. One or more flanges could alternatively extend approximately perpendicular to and along one side of flange 1030, thereby forming in conjunction with flange 1030 an "L" shape. First lamina engaging portion 1020 could also be provided with a "C" shape, such as discussed below with respect to FIGS. 16-19.

Figure 15:
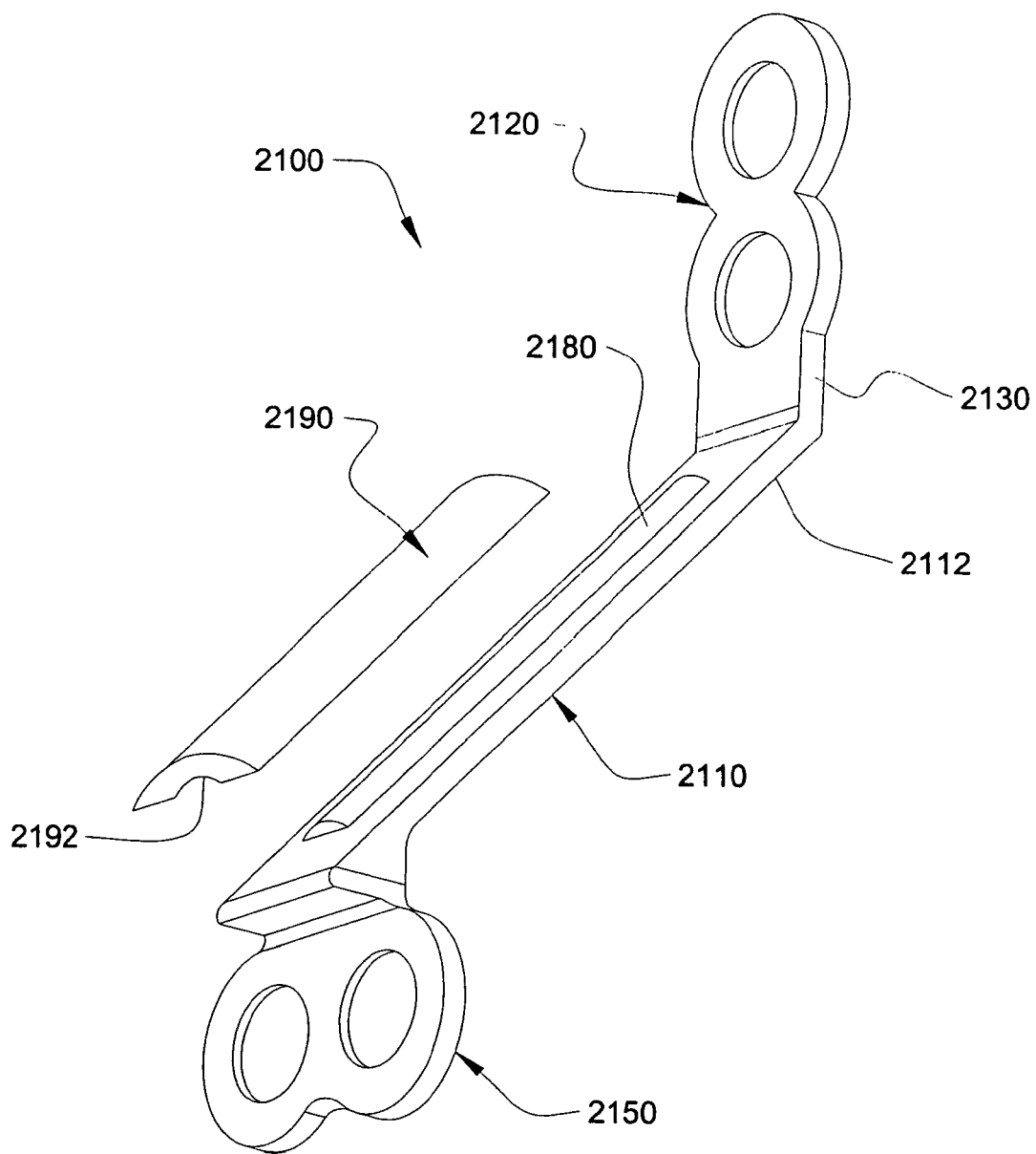
FIG. 15 is a perspective view of another embodiment laminoplasty plate.

Referring to FIG. 15, there is shown laminoplasty plate 2100. Except as noted, plate 2100 can be similar to plate 1000 discussed above. Plate 2100 includes a spacer portion 2110 with a second lamina engaging portion 2150 that can be similar to second lamina engaging portion 1050 discussed above. Adjacent first end 2112 of spacer portion 2110 is a first engaging portion 2120, which can include a single flange 2130, although other flange arrangements are also contemplated. At least one restraining member 2180 is provided extending from an anteriorly oriented surface of spacer portion 2110. In certain embodiments, spacer member 2190 can be shaped to receive restraining member 2180, such as for example, by providing spacer member 2190 with a groove 2192 that corresponds to, for example, a rib-like restraining member 2180. Restraining member 2180 can include any form that resists relative movement between spacer portion 2110 and one or more adjacent spacer members 2190, including, for example, one or more ribs, splines, webs, grooves, teeth, spikes, peaks, valleys, anchor, and/or roughened surfaces.

Figure 16:
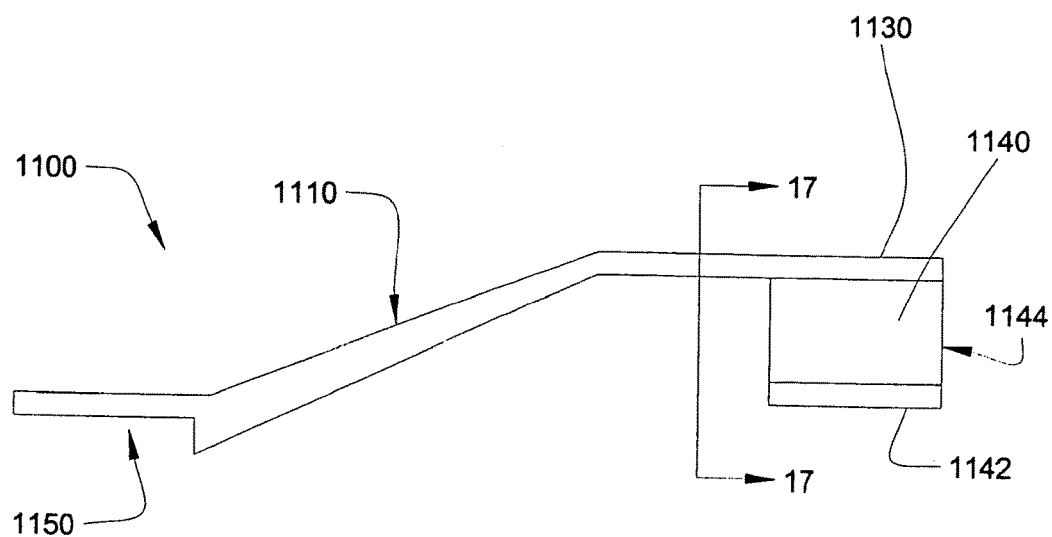
FIG. 16 is an elevation view of yet another embodiment laminoplasty plate.
Figure 17:
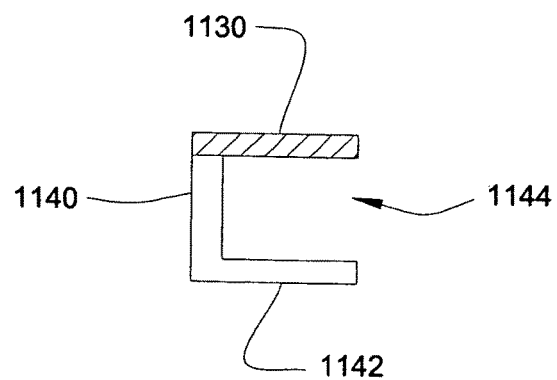
FIG. 17 is a section view along line 17-17 of FIG. 16.

FIG. 16 is a side view of another embodiment laminoplasty plate 1100 that can be employed, for example, with a hemilateral open door laminoplasty system, although application with other laminoplasty procedures is contemplated. Plate 1100 can include a spacer portion 1110 and a second lamina engaging portion 11150 that can be similar to spacer portion 1010 and second lamina engaging portion 1050 discussed above for plate 1000. Plate 1100 includes a first lamina engaging portion 1144 having a second flange 1140 extending perpendicularly to a first flange 1130. A third flange 1142 extends perpendicularly to second flange 1140 and generally parallel to first flange 1130. As shown in FIG. 17, flanges 1130, 1140, 1142 form a generally "C" shape to receive a portion of the divided lamina along its anterior, posterior and inferior surfaces. Accordingly, the posterior surface of the divided lamina can be in contact with or engaged with first flange 1130. Second flange 1140 can contact or engage the divided lamina portion on its bottom or inferior surface. Third flange 1142 can engage or contact the divided lamina portion on its anterior surface. Other embodiments contemplate that that second flange 1140 is positioned along the superior surface of the divided lamina portion.

Figure 18:
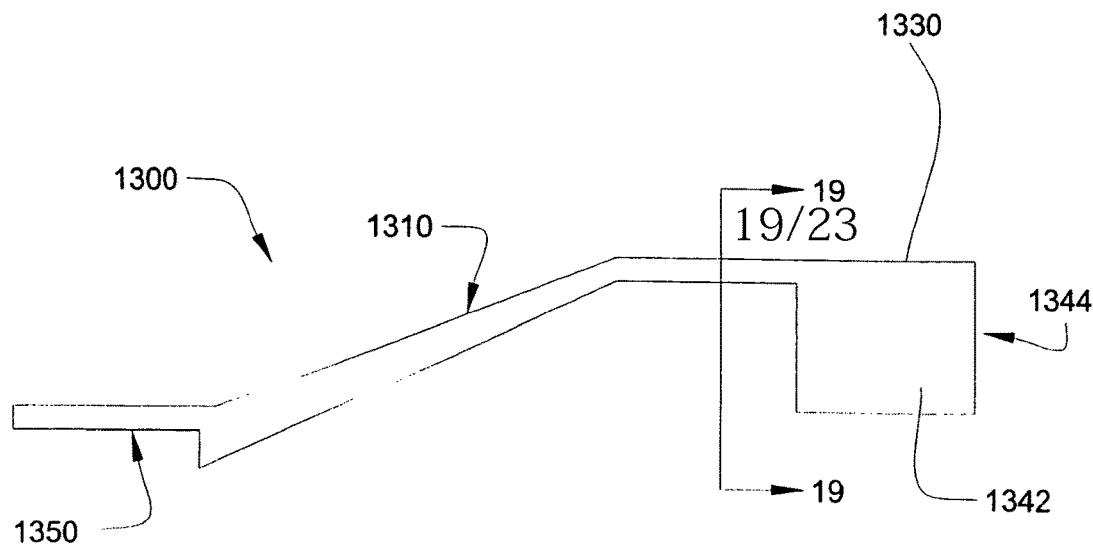
FIG. 18 is an elevation view of another embodiment laminoplasty plate.
Figure 19:
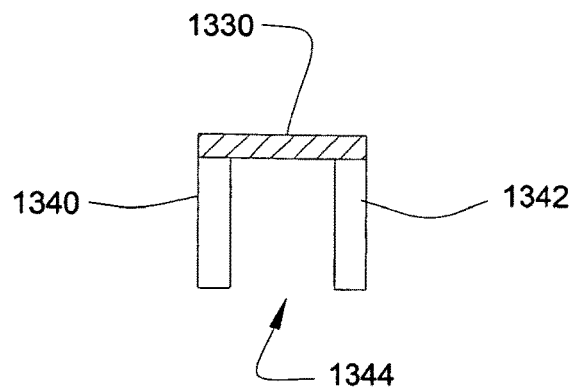
FIG. 19 is a section view along line 19-19 of FIG. 18.

FIG. 18 is a side view of another embodiment laminoplasty plate 1300 that can be employed, for example, with a hemilateral open door laminoplasty system, although application with other laminoplasty procedures is contemplated. Plate 1300 can include a spacer portion 1310 and a second lamina engaging portion 1350 that can be similar to spacer portion 1010 and second lamina engaging portion 1050 discussed above for plate 1000. Plate 1300 includes a first lamina engaging portion 1344 having a second flange 1342 extending perpendicularly to first flange 1330. A third flange 1340 extends perpendicularly to first flange 1330 and generally parallel to second flange 1342. As shown in FIG. 19, flanges 1330, 1340 and 1342 form generally a "C" shape to receive the a portion of the divided lamina. Accordingly, the superior surface of the divided lamina portion can be in contact with or engaged to second flange 1342, the inferior surface of the divided lamina portion can be in contact with or engaged to third flange 1340, and first flange 1330 can be in contact with the posterior surface of the divided lamina portion.

The illustrated embodiments of the first lamina engaging portions in FIGS. 16-19 illustrate a rectangular "C" shape. Other embodiments contemplate interior surface profiles for the flanges of the lamina engaging portion that include rounded, circular, oval, non-circular, or polygonal interior surface profiles.

Figure 20:
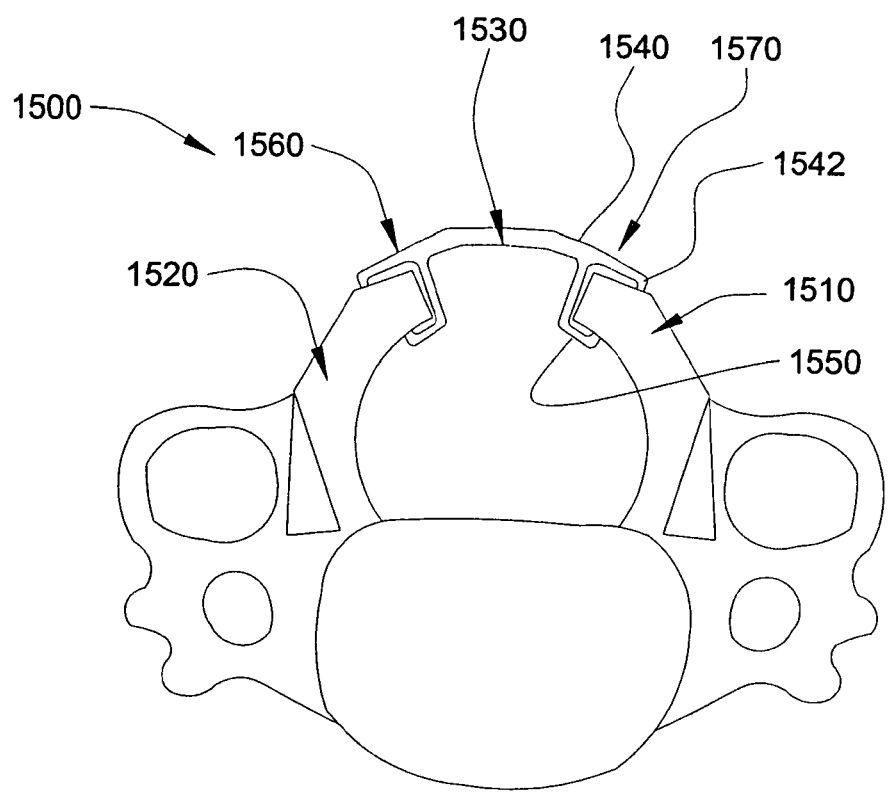
FIG. 20 is a plan view of a vertebra having a French door laminoplasty and another embodiment of a laminoplasty plate secured to the vertebra.

FIG. 20 is a plan view of a vertebra that has been subjected to a French door laminoplasty procedure. The spinous process has been removed, and hinges have been formed in each lamina, and/or between each lamina and its respective facet. The hinged laminae are shown secured in their respective open positions by a laminoplasty plate 1500 for a French door laminoplasty procedure.

First lamina portion 1510 is held apart a predetermined distance from second lamina portion 1520 by spacer portion 1530 of plate 1500. The longitudinal length of spacer portion 1530 can correspond to a desired separation distance between first lamina portion 1510 and second lamina portion 1520. Spacer portion 1530 can have sufficient structural strength to shield the spine and/or spinal canal in a manner approximately equivalent to, and/or better than, the previous bone structure.

Adjacent one end of spacer portion 1530 is a first lamina engagement portion 1570, and adjacent the other end of spacer portion 1530 is a second lamina engagement portion 1560. First lamina engagement portion 1570 includes a first plurality of lamina engagement flanges 1540 and 1550 for engagement with first lamina portion 1510. Flanges 1540, 1550 can be positioned and/or distributed about first lamina portion 1510 to engage at least two surfaces thereof which, in the illustrated embodiment, include the anterior and posterior surfaces. Lamina portion 1510 can be received between flanges 1540, 1550 so that lamina portion 1510 is at least partially captured or located therebetween. Securement holes can be provided through any flange 1540, 1550 to receive a securement mechanism. One or more bone engagement mechanisms 1542 can be provided on one or both of the flanges 1540, 1550 to grasp, grip, engage, crimp, clamp, capture, and/or restrain the lamina portion 1510 relative to plate 1500. Second lamina engagement portion 1560 can be configured similarly to first lamina engagement portion 1570.

Figure 21:
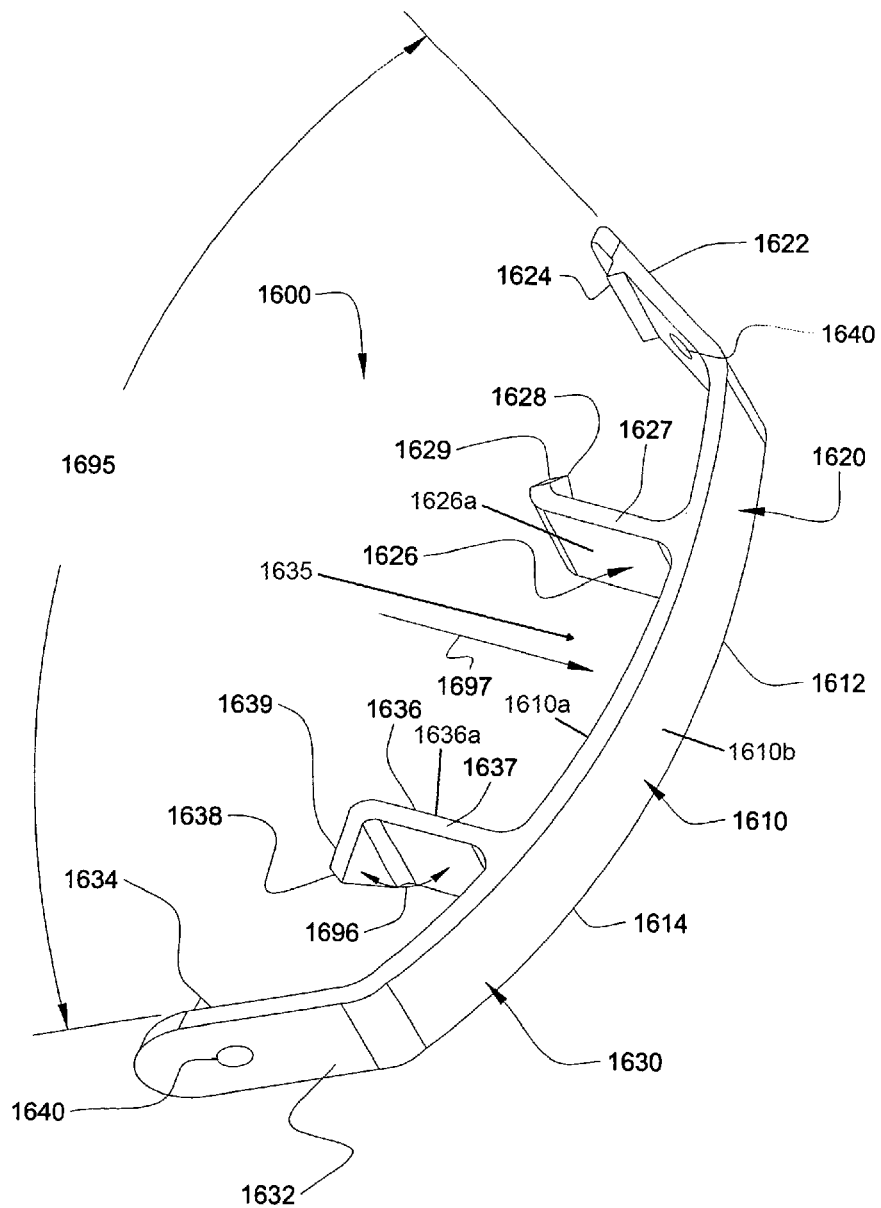
FIG. 21 is a perspective view of another embodiment laminoplasty plate.

FIG. 21 is a perspective view of another embodiment laminoplasty plate 1600 for a French door laminoplasty procedure, although application with other laminoplasty procedures is contemplated. Laminoplasty plate 1600 can prevent potential impingement on the spinal cord by either and/or both of the divided laminae of a particular vertebra subject to a French door laminoplasty. Plate 1600 includes a non-threaded spacer portion 1610 having a first end 1612 and a second end 1614. Spacer portion 1610 includes an inner surface 1610a and an opposite outer surface 1610b. Ends 1612 and 1614 can be longitudinally opposed on spacer portion 1610. First lamina engagement portion 1620 is adjacent first end 1612, and second lamina engagement portion 1630 is adjacent second end 1614.

First lamina engagement portion 1620 can include a first lateral flange 1622 and a first medial flange 1626 forming a first bone grasping portion therebetween. An inner surface 1626a of first medial flange 1626, an inner surface 1636a of second medial flange 1636 that faces inner surface 1626a of first medial flange 1626, and inner surface 1610a of spacer portion 1610 define a cavity 1635. As shown in FIG. 21, first medial flange 1626 extends from inner surface 1610a of spacer portion 1610. First lateral flange 1622 can also include one or more inwardly facing bone engagement mechanisms 1624. First medial flange 1626 can include one or more second lamina engagement flanges, such as, for example, outward facing bone engagement mechanisms 1628 that extend in a first direction from a tip of first medial flange 1626. Thus, a pair of opposed bone engagement mechanisms can be supplied by flanges 1622, 1626. Bone engagement mechanisms 1624, 1628 can have similar or different geometric configurations. For example, either of engagement mechanisms 1624, 1628 can be configured to contact a remaining portion of a divided lamina portion along a line of contact, as shown for mechanism 1624, at multiple points of contact, or at a single point of contact as shown for mechanism 1628. Once such contact is made, the mechanism can bite into or grip the divided lamina portion.

Second lamina engagement portion 1630 can include a second lateral flange 1632 and a second medial flange 1636 forming a second bone grasping portion therebetween. As shown in FIG. 21, second medial flange 1636 extends from inner surface 1610 of spacer portion 1610. Second lateral flange 1632 can include one or more inwardly facing bone engagement mechanisms 1634. Second medial flange 1636 can include one or more second lamina engagement flanges, such as, for example, outward facing bone engagement mechanisms 1638 that extend in a second direction that is opposite the first direction from a tip of second medial flange 1636 such that flange 1638 faces away from flange 1628. Thus, a pair of opposed bone engagement mechanisms can be supplied by flanges 1632, 1636. Bone engagement mechanisms 1634, 1638 can have similar or different geometric configurations. For example, either of engagement mechanisms 1634, 1638 can be configured to contact a divided lamina portion along a line of contact, as shown for mechanism 1634, at multiple points of contact, or at a single point of contact as shown for mechanism 1638. Once such contact is made, the engagement mechanism can bite into and/or grip the divided lamina portion.

Second lamina engagement portion 1630 can be symmetrical to first lamina engagement portion 1620. Spacer portion 1610, first engagement portion 1620, second engagement portion 1630, and/or any flange 1622, 1626, 1632, and/or 1636 can include one or more securement openings 1640 to accommodate securement mechanisms. As viewed superiorly when installed, spacer portion 1610 extends between the remaining divided laminae across the location of the removed spinous process, thereby maintaining a cross-sectional area of the spinal canal and providing a structural replacement for the removed bone.

First lateral flange 1622 of first lamina engagement portion 1620 can contact a laterally or posteriorly facing outer surface of a divided lamina portion. Likewise, the first medial flange 1626 can contact a medially or anteriorly facing inner surface of the divided lamina portion. Flanges 1622, 1626 can be crimped and/or squeezed together to engage bone engagement mechanism 1624, 1628 with the divided lamina portion positioned therebetween, thereby clamping the divided lamina portion and preventing its movement and/or the closing of the first French door.

Likewise, as viewed superiorly when installed, the second lateral flange 1632 of second lamina engagement portion 1630 can contact a laterally or posteriorly facing outer surface of a second divided lamina portion. The second medial flange 1636 can contact a medially or anteriorly facing inner surface of the second divided lamina portion. Flanges 1632, 1636 can be crimped and/or squeezed together to engage bone engagement teeth 1634, 1638 with the second divided lamina portion therebetween, thereby clamping the second divided lamina and preventing its movement and/or the closing of the divided laminae.

In an alternative embodiment (not shown), first lamina engagement portion 1620 can include a superior flange and a subjacent flange. The superior flange can be adapted to contact a superior surface of the first divided lamina portion. Second lamina engagement portion 1630 can be configured similarly. Alternatively, a "C" shape or enclosed shape arrangement can be utilized for one or both lamina engagement portions 1620, 1630.

A spacer member can be inserted between the first and second divided laminae. Such a spacer member can be secured via securement mechanism extending through securement holes (not shown) in spacer portion 1610, first lamina engagement portion 1620, first lateral flange 1622, first medial flange 1626, second lamina engagement portion 1630, second lateral flange 1632, and/or second medial flange 1636. Thus, the spacer member can be held between the first and second divided laminae, and the ends of the laminae can be secured with respect to each other to prevent them from pulling apart. In applications where the spacer member is a fusion member, contact between the ends of the divided laminae and the fusion member can be maintained and protected by plate 1600, promoting fusion.

First and second lateral flanges 1622, 1632 subtend an angle 1695, and spacer portion 1610 can be curved along a radius 1697. In one specific embodiment, angle 1695 is about 53 degrees, and radius 1697 is about 21 millimeters. Other embodiments contemplate angle 1695 ranging from 40 to 65 degrees, or from 0 degrees or less to 180 degrees or more. Other embodiments further contemplate other radii 1697 for spacer portion 1610. Also contemplated are spacer portions 1610 that are not curved, but rather are straight or comprise a series of angularly offset linear portions or a series of curved portions.

Medial flanges 1626, 1636 can extend parallel to one another as shown. Other embodiments contemplate that medial flanges 1626, 1636 diverge or converge relative to one another as they extend from spacer portion 1610. Medial flanges 1626, 1636 can each include a connecting portion 1627, 1637, respectively, and an end portion 1629, 1639, respectively. End portions 1629, 1639 extend from connecting portions 1627, 1637, respectively. In one embodiment, connecting portion 1637 forms an angle 1696 with end portion 1639. Similarly, connecting portion 1627 may form an angle with end portion 1629. In one specific embodiment, angle 1696 is about 120 degrees. Other embodiments contemplate other values for angle 1696.

Figure 22:
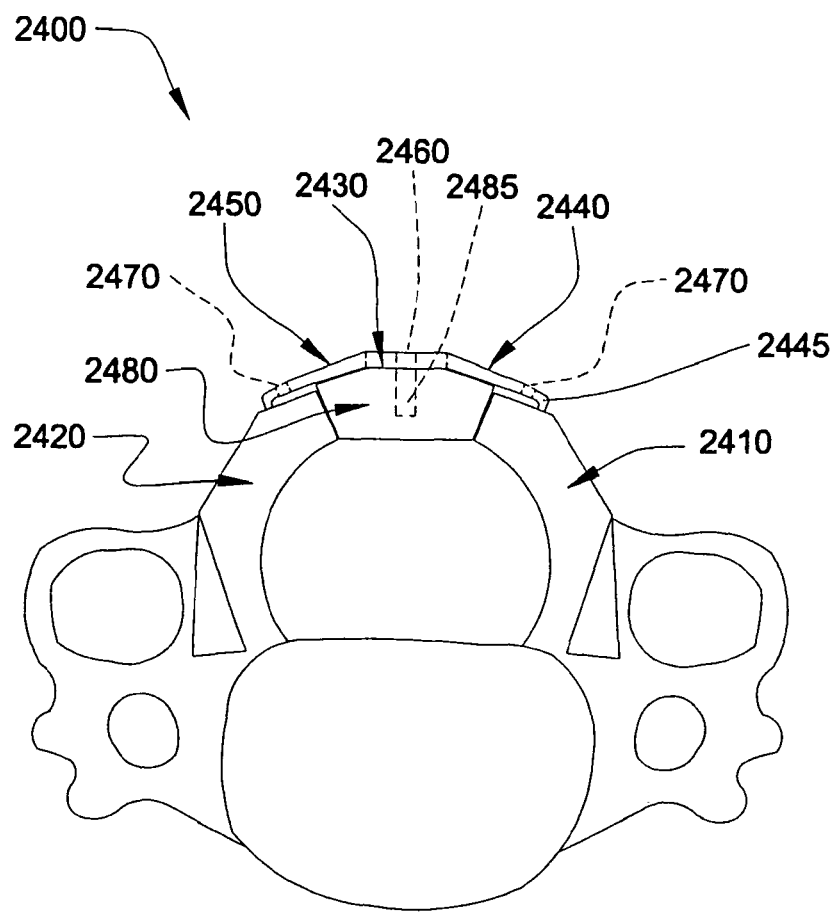
FIG. 22 is a plan view in partial section of a vertebra having a French door laminoplasty and another embodiment of a laminoplasty plate secured to the vertebra.

FIG. 22 is a plan view of another embodiment laminoplasty plate 2400 similar to plate 1500 of FIG. 20 and plate 1600 of FIG. 21. Plate 2400 can include a spacer portion 2430 having a first lamina engaging portion 2440 adjacent one end and a second lamina engaging portion 2450 adjacent its other end. One or more securement openings 2460 are provided in spacer portion 2430, and one or more securement openings 2470 are provided in each engagement portion 2440, 2450. Securement openings 2460, 2470 can allow one or more securement mechanisms (not shown), to be inserted into the underlying lamina portions 2410, 2420 and/or spacer member 2480 and secure laminoplasty plate 2400 relative to the lamina portions 2410, 2420 and/or spacer member 2480. Securement openings 2460, 2470 may further comprise a slot to permit variable orientation and placement of securement mechanisms relative to the underlying lamina portions 2410, 2420 and/or spacer member 2480.

Figure 23:
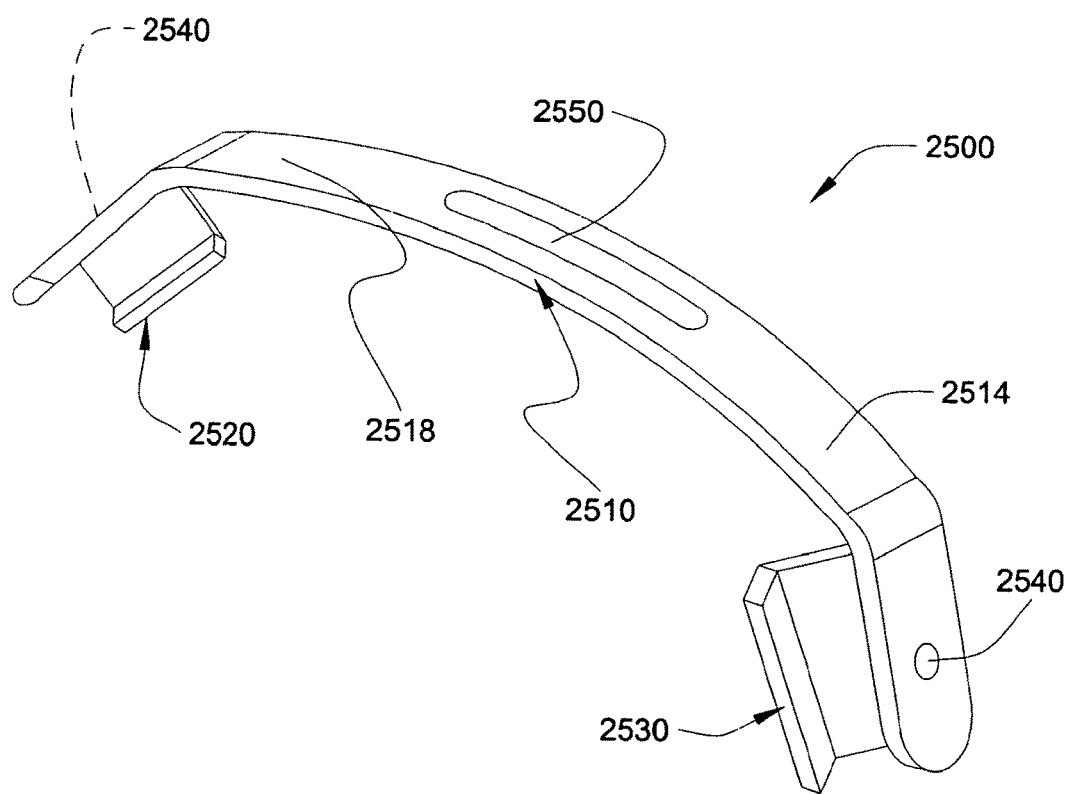
FIG. 23 is a perspective view of another embodiment laminoplasty plate.

FIG. 23 is an elevational side view of an alternative embodiment of the laminoplasty plate 1600 of FIG. 21. Laminoplasty plate 2500 includes a spacer portion 2510 and lamina engagement portions 2530, 2520 adjacent first and second end 2514, 2518, respectively. Securement opening 2550 in spacer portion 2510 may further comprise a slot to permit variable orientation and placement of the laminoplasty plate relative to the underlying spacer member. Engagement portions 2520, 2530 each include a plurality of flanges for engagement with the adjacent lamina portion. Lamina engagement portions 2520, 2530 each include a "C" shape for engagement with the anterior and posterior surfaces of the respective lamina portion, and also for engagement with one of the superior or inferior surfaces of the lamina portion. Securement openings 2540 in engagement portions 2520, 2530 can allow one or more securement mechanisms (not shown) to be inserted into the underlying lamina portion. The open ends of each of the C-shaped lamina engagement portions allow for full surface area contact between a bone spacer positioned along spacer portion 2510 and the adjacent lamina portion.

In another embodiment, on at least one end of the plate 2500, the flanges can be replaced with a lamina engaging cup or annulus that completely or substantially surrounds an end of the divided lamina. Such a cup could advantageously reduce, restrain, and/or prevent radial movement of the end of the divided lamina portion up to 360 degrees about an axis of the lamina, thereby further facilitating fusion and protection of the spinal canal. The cup could be crimped onto the end of the divided lamina portion for secure engagement therewith. Also, the cup could be lined and/or formed with one or more bone engagement mechanisms, such as for example, teeth, splines, threads, and/or grooves, for engagement with the lamina portion. The cup could include one or more securement openings through which a securement mechanism could be inserted to couple the cup and the underlying lamina portion. Further, the cup could include a bone ingrowth surface and/or a bone growth-inducing material.

Figure 24:
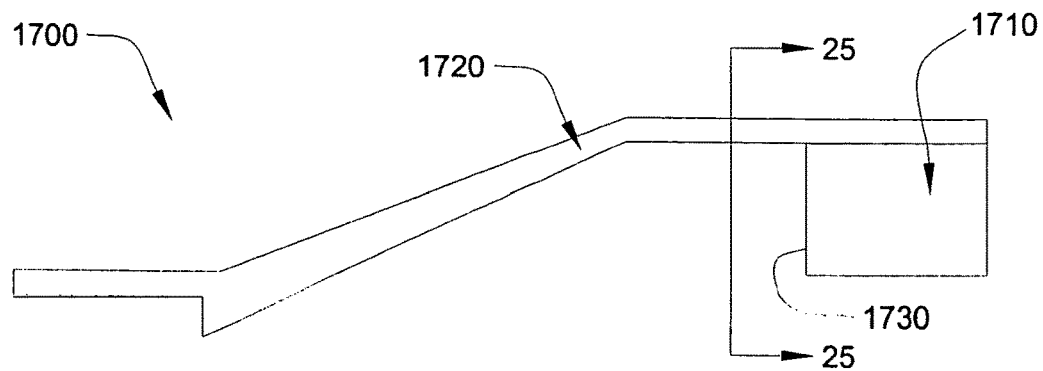
FIG. 24 is an elevation view of another embodiment laminoplasty plate.
Figure 25:
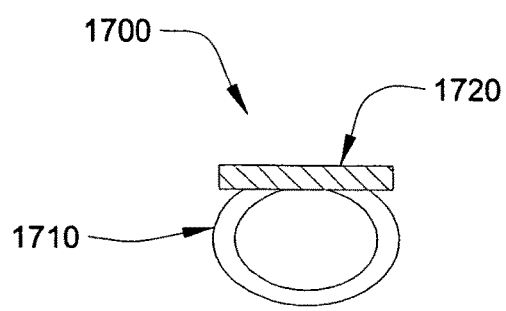
FIG. 25 is a section view along line 25-25 of FIG. 24.

A further example of a laminoplasty plate having a lamina engagement cup is shown in FIGS. 24 and 25. Except as noted, laminoplasty plate 1700 can be similar to laminoplasty plate 800 of FIGS. 8, 9 and 10. Laminoplasty plate 1700 includes a lamina engaging cup 1710 at an end of spacer portion 1720. Cup 1710 can be bottomless, so that it resembles an elongated annulus, closed polygon, or an "O" shaped receptacle. The cross-section of cup 1710 can be any closed polygon, and thus can be circular, elliptical, racetrack shaped, rectangular, polygonal, etc. Moreover, the cross-section of the lamina can be shaped during surgery to fit within or provide a desired fit with a particular shape for cup 1710.

Cup 1710 can also be provided with a bottom surface 1730 medially oriented with respect to spacer portion 1720. An open bottom surface 1739 for cup 1710 can be desirable in procedures where fusion between the divided lamina portions is sought. The walls of cup 1710 can be adapted to slidably extend over both an end of the lamina and over the end of the spacer member, providing one or more contact points, lines, and/or surfaces between cup 1710 and the underlying lamina portion and the spacer member. Further, cup 1710 can be adapted to contact, engage, grasp, and/or crimp both the lamina portion and the spacer member positioned therein, further resisting relative movement therebetween. In certain embodiments, plate 1700 and/or cup 1710 can be constructed of a resorbable material so that once fusion has occurred between the end of the divided lamina and the adjacent spacer member, plate 1700 and/or cup 1710 are resorbed.

Figure 26:
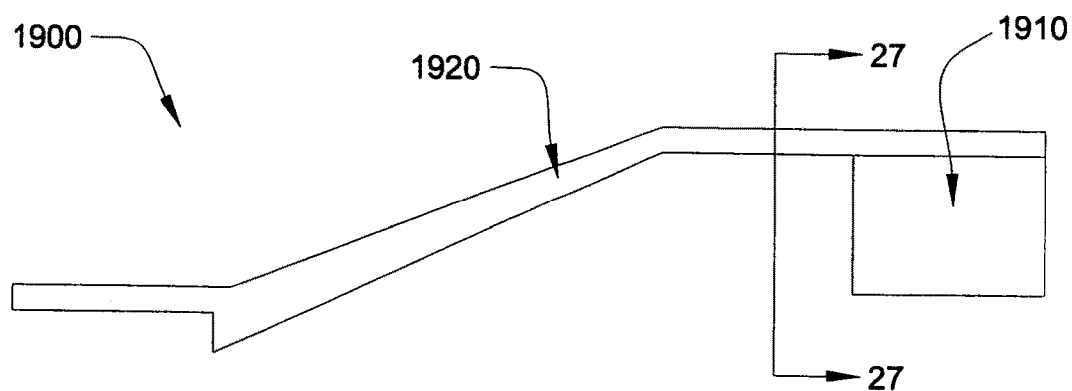
FIG. 26 is an elevation view of another embodiment laminoplasty plate.
Figure 27:
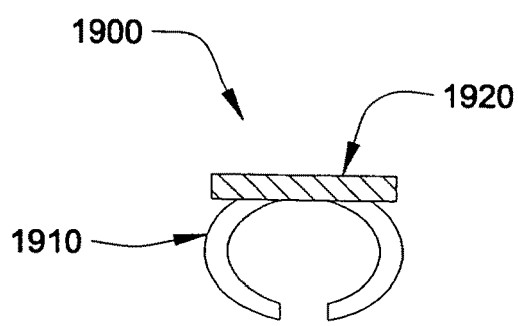
FIG. 27 is a section view along line 27-27 of FIG. 26.

As a further exemplary embodiment, an adjustable cuff 1910, as shown in FIGS. 26 and 27, is provided with laminoplasty plate 1900 and attached to an end of spacer portion 1920. Except as noted, laminoplasty plate 1900 can be similar to laminoplasty plate 800 of FIGS. 8, 9 and 10. Cuff 1910 can be similar to cup 1710, however the cross-section of cuff 1910 defines any open polygonal shape or curved shape. The walls of adjustable cuff 1910 can also be spread apart and adjusted to fit the bone of the underlying lamina portion. Cuff 1910 can thus be side-loaded onto the divided lamina portion by separating the arms of cuff 1910. Moreover, the cross-section of the lamina can be shaped to fit within a particular shaped cuff 1910. The gap between the arms of cuff 1910 can also be positioned for top or bottom loading on the divided lamina portion. Cuff 1910 can be spring biased to return toward its natural state, and when separated and placed around the lamina portion, can clamp the lamina portion for engagement therewith. Cuff 1910 and/or the divided lamina portion can also be sized so that a clamping force is not delivered to the divided lamina portion. Whether clamped or not clamped, engagement mechanisms and/or securement openings for securement mechanisms can be provided to engage cuff 1910 to the divided lamina portion.

Figure 28:
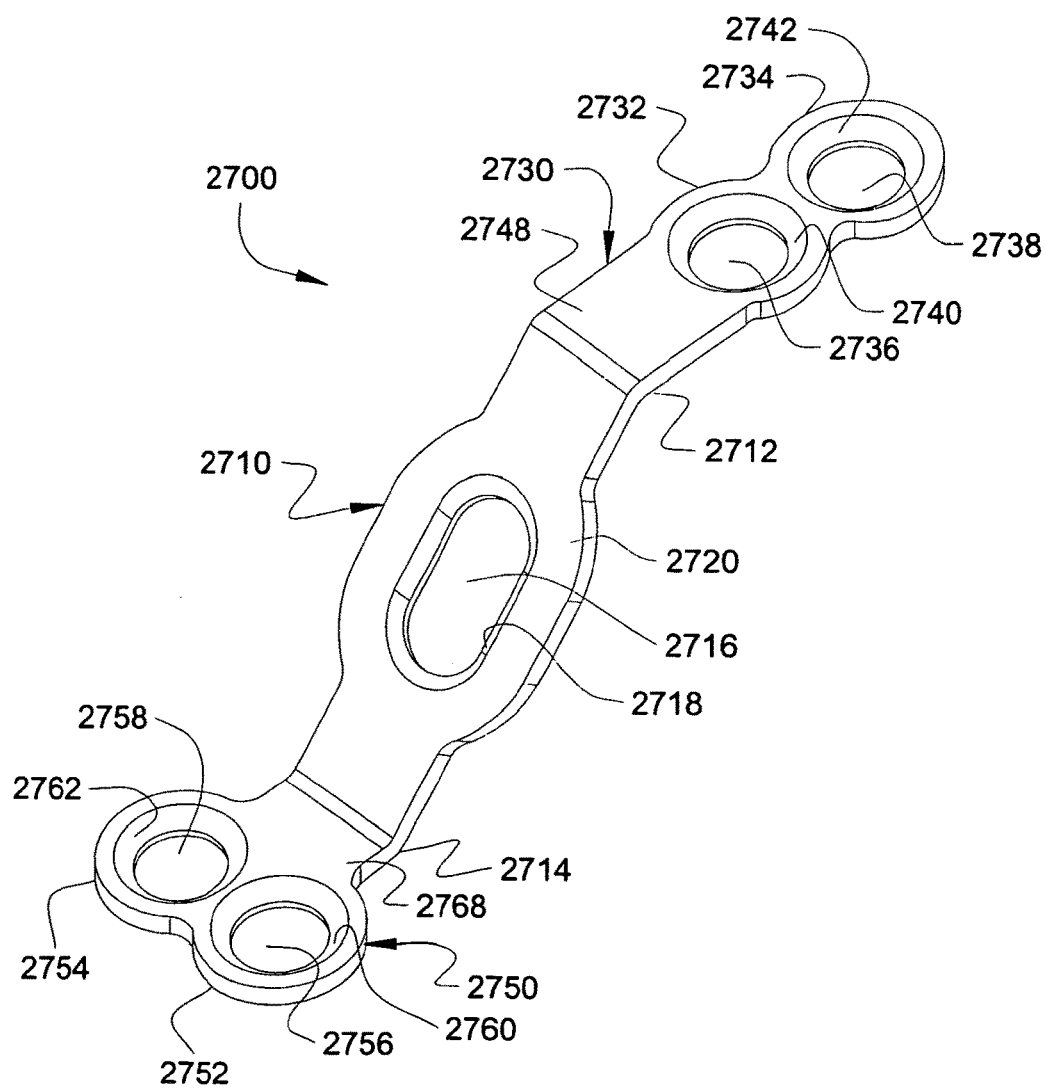
FIG. 28 is a perspective view of another embodiment laminoplasty plate as viewed from the posterior side.
Figure 29:
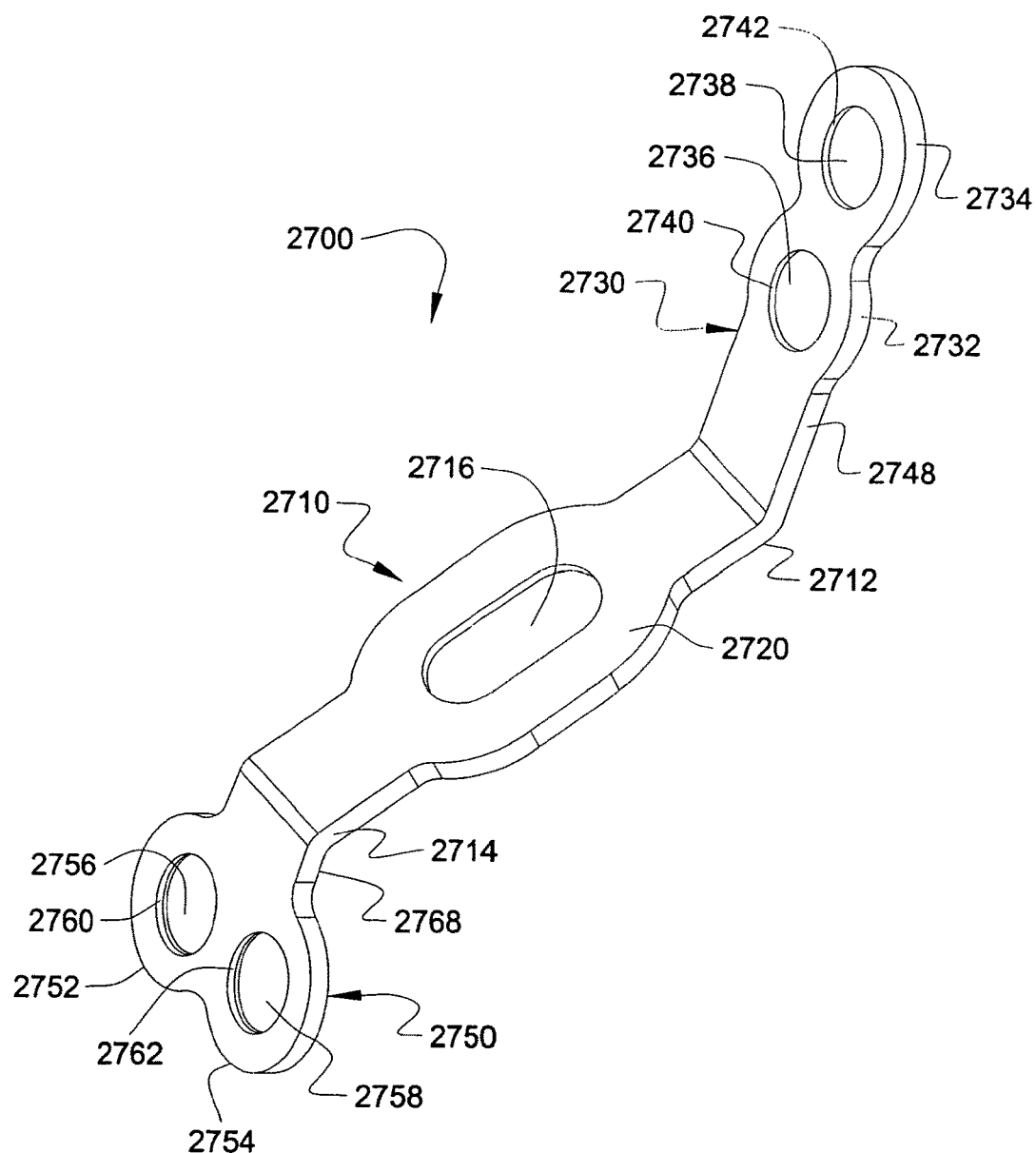
FIG. 29 is a perspective view of the anterior side of the laminoplasty plate of FIG. 28.

FIGS. 28 and 29 are perspective views of another embodiment laminoplasty plate. Laminoplasty plate 2700 is particularly suited for a hemilateral open door laminoplasty procedure, although application with other laminoplasty procedures is contemplated. Plate 2700 includes a spacer portion 2710 extending between a first end 2712 and a second end 2714. Spacer portion 2710 includes a slotted securement opening 2716. Securement opening 2716 can have a recessed portion 2718 adjacent the posteriorly oriented surface of spacer portion 2710. Recessed portion 2718 allows a securement mechanism to be at least partially recessed therein for a lower profile relative to spacer portion 2710. Recessed portion 2718 can also include a spherical profile to mate with a spherical surface of securement mechanism for variable angle placement of the securement mechanism relative to spacer portion 2710. Spacer portion 2710 can have an enlarged portion 2720 with a greater width around securement opening 2716 to accommodate securement opening 2716 while minimizing the width of spacer portion 2710 adjacent first end 2712 and second 2714. Enlarged portion 2720 provides stiffness to spacer portion 2710, while the reduced width at ends 2712, 2714 facilitate bending of lamina engagement portions 2712, 2714.

Adjacent first end 2712 is first lamina engagement portion 2730. Lamina engagement portion 2730 includes first node 2732 and second node 2734. Nodes 2732, 2734 are aligned along an axis of a first flange 2748 extending from first end 2712. Nodes 2732, 2734 can be enlarged relative to first flange 2748 to accommodate respective ones of securement openings 2736, 2738. Securement opening 2736 can have a recessed portion 2740 adjacent the outwardly facing surface of first node 2732. Recessed portion 2740 allows a securement mechanism to be at least partially recessed therein for a lower profile relative to first flange 2748. Securement opening 2738 can have a recessed portion 2742 adjacent the outwardly facing surface of second node 2734. Recessed portion 2742 allows a securement mechanism to be at least partially recessed therein for a lower profile relative to first flange 2748. Recessed portions 2740, 2742 can also have a spherical profile to mate with a spherical surface of a securement mechanism positioned therein for variable angle placement of the securement mechanism relative to first flange 2748.

Adjacent second end 2714 is a second lamina engagement portion 2750. Lamina engagement portion 2750 includes a second flange 2768 having a first node 2752 and a second node 2754. First and second flanges 2748, 2768 can be arranged relative to spacer portion 2710 in a manner similar to that discussed above with respect to plate 800 of FIGS. 8, 9 and 10. Nodes 2752, 2754 are aligned along an axis that extends transversely to the longitudinal axis of second flange 2768. Nodes 2752, 2754 can be enlarged relative to flange 2768 to accommodate respective ones of securement openings 2756, 2758. Securement opening 2756 can have a recessed portion 2760 adjacent the outwardly facing surface of first node 2752. Recessed portion 2760 allows a securement mechanism to be at least partially recessed therein for a lower profile relative to flange 2768. Securement opening 2758 can have a recessed portion 2762 adjacent the outwardly facing surface of second node 2754. Recessed portion 2762 allows a securement mechanism to be at least partially recessed therein for a lower profile relative to second flange 2768. Recessed portions 2760, 2762 can also have a spherical profile to mate with a spherical surface of securement mechanism for variable angle placement of the securement mechanism relative to second flange 2768.

In a further form of the plates discussed hereinabove, the number of flanges of at least one of the lamina engagement portions of the laminoplasty plates can be increased to provide additional points, lines, and/or surfaces of contact between the engagement portion and the divided lamina portion. The flanges can be distributed about the perimeter, or exterior surfaces of the divided lamina portion. Also, the flanges can be distributed evenly or unevenly about the perimeter of the divided lamina. Moreover, the distribution can be about a longitudinal axis of the divided lamina, about a line parallel to a longitudinal axis of the spacer portion, and/or about a line parallel to a longitudinal axis of the laminoplasty plate. Furthermore, one or more of the flanges can be flat and/or curved to accommodate the curvature of the outer surface of the divided lamina. The flanges can at least partially engage the divided lamina portion by contacting, attaching to, crimping or clamping about, and/or gripping the underlying lamina portion.

Figure 30:
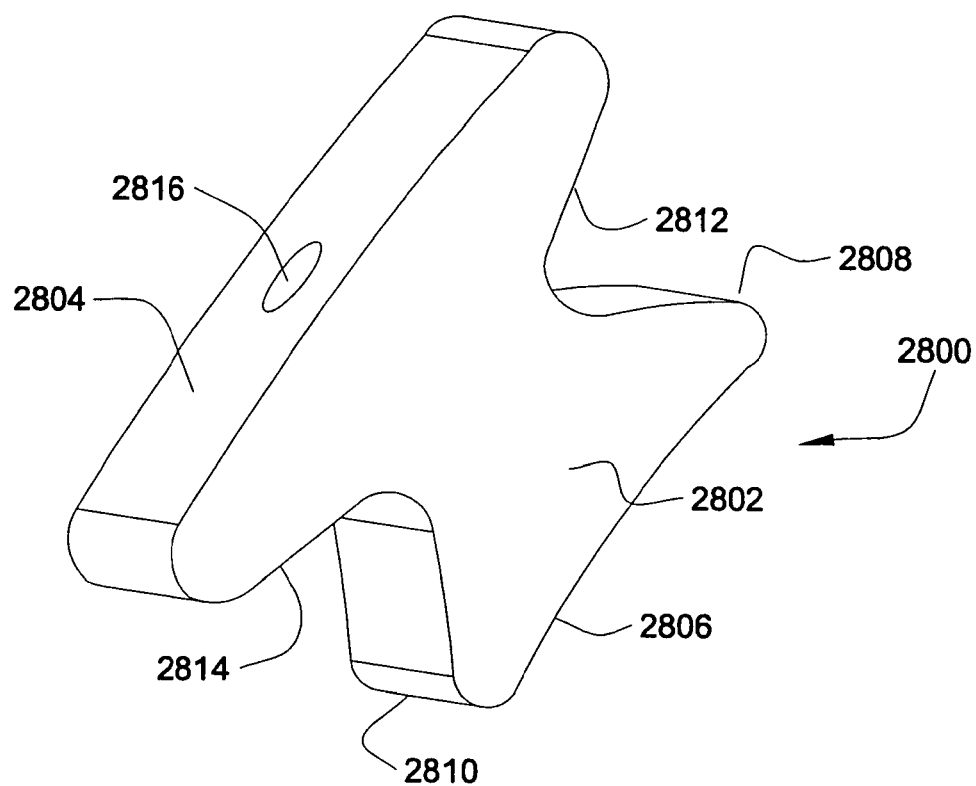
FIG. 30 is a perspective view of a spacer member.

FIG. 30 is a perspective view of a spacer member positionable between divided lamina portions. Spacer member 2800 includes a body 2802 extending between, in one operative orientations, a posterior surface 2804 and an anterior surface 2806. Body 2802 further includes a first end 2808 and a second end 2810. First end 2808 includes a concave surface that forms a first receptacle 2812 for at least partially receiving a first portion of a divided lamina. Similarly, second end 2810 includes a concave surface that forms a second receptacle 2814 for at least partially receiving a second portion of a divided lamina. Surfaces 2812, 2814 can be comprised of a continuous curve, a series of curves, a series of linear segments, or a combination of curves and linear segments. In any event, the lamina engagement receptacles 2812, 2814 can receive the adjacent lamina portion. A large contact surface area is provided by surfaces 2812, 2814 to facilitate engagement, and, if spacer member 2800 is a fusion member, a greater surface area for bone ingrowth.

In use, anterior surface 2806 is oriented toward the spinal canal, and posterior surface 2804 is positioned adjacent a laminoplasty plate. A bore 2816 opening at surface 2804 can receive a securement mechanism to secure spacer member 2800 to a laminoplasty plate. Spacer member 2800 can be used with any of the laminoplasty plate embodiments discussed herein. Spacer member 2800 can be attached to the laminoplasty plate and or to the adjacent divided lamina portions. It is also contemplated that spacer member 2800 can be used without a laminoplasty plate, but rather directly attached to the divided lamina portions. In one form, spacer member 2800 is comprised of a material that can be formed or deformed to conform to the profile of the adjacent separation surfaces of the divided lamina portions. Surfaces 2812, 12814 can extend along posterior and anterior surfaces, for example, of the adjacent divided lamina portion to increase the surface area contact and provide a better fit therewith. Spacer body 2802 could also be oriented so that surfaces 2812, 2814 extend along superior and inferior surfaces of the adjacent lamina portion.

The spacer member embodiments discussed herein can be made of any bio-compatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

The laminoplasty plates discussed herein stabilize divided lamina portions to facilitate fusion with a spacer member placed between the divided lamina portions. The harvesting of a bone graft from the hip or pelvis of the patient can be avoided, reducing patient discomfort and pain. Spacer member displacement and/or spacer member malposition can be reduced or eliminated. Also, the possibility of intrusion of the divided lamina into the spinal canal can be reduced or eliminated, thereby reducing and/or eliminating the possibility of spinal cord impingement by either the plates or the spacer member. The increased stability provided by the plates to the divided lamina portions and to the spacer member can also reduce or eliminate the need for post-operative bracing.

The laminoplasty plates discussed herein can be of a unitary construction, such that the spacer portion, lamina engaging portions and/or the flanges can be integral or formed from a single piece of material. Alternative embodiments contemplate that the components of the laminoplasty plate can be non-integral, and can be attached to and/or coupled to other components of laminoplasty plate. The laminoplasty plates can be dimensioned to accommodate the full variety of vertebrae that can be the object of a laminoplasty procedure, and also for multiple levels of laminoplasty along the spinal column. Embodiments of the laminoplasty plates contemplate a bendable spacer portion and/or one or more bendable lamina engagement portions in order to conform to the anatomy of a particular patient. The spacer portions and/or lamina engagement portions can also be pre-bent to accommodate patient anatomy based on pre-operative planning or anatomical considerations encountered during surgery.

The laminoplasty plates can be constructed of any biocompatible material(s) having sufficient strength to maintain the open position of the divided lamina. Suitable materials include certain metals, polymers, ceramics, and/or composites. The laminoplasty plates can also be constructed of a material that is thermosettable, settable, resorbable, radiolucent, and/or bone growth-inducing. In certain specific embodiments, one suitable material is titanium, such as a titanium alloy, for example CP Ti grade 2 alloy. Another suitable material can be a PAEK (polyaryletherketone) compound, particularly a PEEK (polyetheretherketone) compound.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A laminoplasty plate comprising a non-threaded spacer portion extending between a first end defining a first lamina engagement portion and a second end defining a second lamina engagement portion, the first lamina engagement portion comprising a first lamina engagement flange extending transverse to the spacer portion and a second lamina engagement flange extending in a first direction from a tip of the first lamina engagement flange, the first and second lamina engagement flanges forming an angle of 120 degrees, the second lamina engagement portion comprising a first flange lamina engagement flange extending transverse to the spacer portion and a second lamina engagement flange extending in a second direction that is opposite the first direction from a tip of the first lamina engagement flange of the second lamina engagement portion, the tips being spaced apart from the spacer portion by body portions of the first lamina engagement flanges, a tapered end of the second lamina engagement flange of the first lamina engagement portion extending away from the first lamina engagement flange of the second lamina engagement portion, a tapered end of the second lamina engagement flange of the second lamina engagement portion extending away from the first lamina engagement flange of the first lamina engagement portion,
wherein the first end includes a first lateral flange and the second end includes a second lateral flange, the first lamina engagement flanges being positioned between the first and second lateral flanges.

2. A laminoplasty plate as recited in claim 1, wherein the second lamina engagement flange of the first lamina engagement portion extends transverse to the first lamina engagement flange of the first lamina engagement portion and the second lamina engagement flange of the second lamina engagement portion extends transverse to the first lamina engagement flange of the second lamina engagement portion.

3. A laminoplasty plate as recited in claim 1, wherein the first and second lateral flanges each include an inwardly facing bone engagement mechanism.

4. A laminoplasty plate as recited in claim 3, wherein the second lamina engagement flange of the first lamina engagement portion faces the bone engagement mechanism on the first lateral flange and the second lamina engagement flange of the second lamina engagement portion faces the bone engagement mechanism on the second lateral flange.

5. A laminoplasty plate as recited in claim 1, wherein:
the first lamina engagement flange of the first lamina engagement portion is configured to deflect relative to the first lamina engagement flange of the second lamina engagement portion;
the first lateral flange is configured to deflect relative to the first lamina engagement flange of the first lamina engagement portion; and
the second lateral flange is configured to deflect relative to the first lamina engagement flange of the second lamina engagement portion.

6. A laminoplasty plate as recited in claim 1, wherein the second lamina engagement flange of the second lamina engagement portion extends at an angle of 120 degrees relative to the first lamina engagement flange of the second lamina engagement portion.

\* \* \* \* \*